(12) United States Patent
Baxter et al.

(10) Patent No.: US 6,562,825 B1
(45) Date of Patent: May 13, 2003

(54) PIPERAZINE DERIVATIVES AS MODULATORS OF CHEMOKINE RECEPTOR ACTIVITY

(75) Inventors: Andrew J G Baxter, Loughborough (GB); Stephen J Brough, Loughborough (GB); Nicholas D Kindon, Loughborough (GB); Thomas McInally, Loughborough (GB); Bryan Roberts, Loughborough (GB)

(73) Assignee: Astrazeneca UK Limited, London (GB)

( * ) Notice: Subject to any disclaimer, the term of this patent is extended or adjusted under 35 U.S.C. 154(b) by 30 days.

(21) Appl. No.: 09/640,398

(22) PCT Filed: Jun. 27, 2000

(86) PCT No.: PCT/GB00/02470

§ 371 (c)(1),
(2), (4) Date: Aug. 17, 2000

(87) PCT Pub. No.: WO01/02381

PCT Pub. Date: Jan. 11, 2001

(30) Foreign Application Priority Data

Jul. 2, 1999 (SE) .............................................. 9902551

(51) Int. Cl.[7] ..................... A61K 31/495; C07D 295/13; C07D 295/185; C07D 295/155
(52) U.S. Cl. ................................... 514/252.12; 544/400
(58) Field of Search ....................... 544/400; 514/252.12

(56) References Cited

FOREIGN PATENT DOCUMENTS

| EP | 496691 A1 | * | 7/1992 |
| EP | 903349 A2 | * | 3/1999 |

OTHER PUBLICATIONS

Trivedi et al. in "Annual Reports in Medicinal Chemistry", vol. 35, pp. 191–200 (2000).*

* cited by examiner

Primary Examiner—Richard L. Raymond
(74) Attorney, Agent, or Firm—Fish & Richardson P.C.

(57) ABSTRACT

The invention provides compounds of general formula (I)

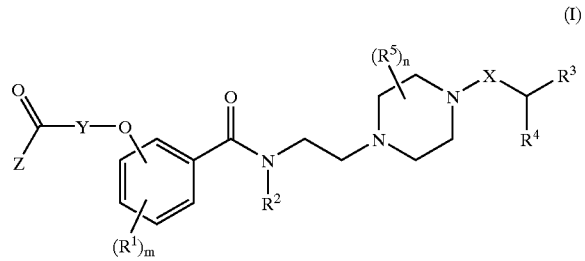

wherein $R^1$, $R^2$, $R^3$, $R^4$, $R^5$, X, Y, Z, m and n are as defined in the specification, processes for their preparation, pharmaceutical compositions containing them and their use in therapy, especially for the treatment of chemokine receptor related diseases and conditions.

11 Claims, No Drawings

PIPERAZINE DERIVATIVES AS MODULATORS OF CHEMOKINE RECEPTOR ACTIVITY

This application is a 371 of PCT/GB00/02470, filed Jun. 27, 2000.

FIELD OF THE INVENTION

The present invention relates to novel compounds, processes for their preparation, pharmaceutical compositions containing them and their use in therapy.

BACKGROUND OF THE INVENTION

Chemokines play an important role in immune and inflammatory responses in various diseases and disorders, including asthma and allergic diseases, as well as autoimmune pathologies such as rheumatoid arthritis and atherosclerosis. These small secreted molecules are a growing superfamily of 8–14 kDa proteins characterised by a conserved four cysteine motif. The chemokine superfamily can be divided into two main groups exhibiting characteristic structural motifs, the Cys-X-Cys (C-X-C) and Cys-Cys (C-C) families. These are distinguished on the basis of a single amino acid insertion between the NH-proximal pair of cysteine residues and sequence similarity.

The C-X-C chemokines include several potent chemoattractants and activators of neutrophils such as interleukin-8 (IL-8) and neutrophil-activating peptide 2 (NAP-2).

The C-C chemokines include potent chemoattractants of monocytes and lymphocytes but not neutrophils such as human monocyte chemotactic proteins 1–3 (MCP-1, MCP-2 and MCP-3), RANTES (Regulated on Activation, Normal T Expressed and Secreted), eotaxin and the macrophage inflammatory proteins 1α and 1β (MIP-1α and MIP-1β).

Studies have demonstrated that the actions of the chemokines are mediated by subfamilies of G protein-coupled receptors, among which are the receptors designated CCR1, CCR2, CCR2A, CCR2B, CCR3, CCR4, CCR5, CCR6, CCR7, CXCR1, CXCR2, CXCR3 and CXCR4. These receptors represent good targets for drug development since agents which modulate these receptors would be useful in the treatment of disorders and diseases such as those mentioned above.

EP 0 903 349 (Hoffmann-La Roche) discloses compounds of general formula

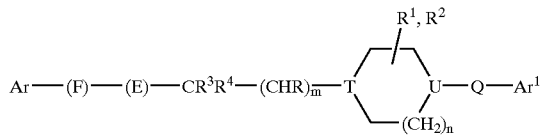

that are CCR-3 receptor antagonists.

DISCLOSURE OF THE INVENTION

In accordance with the present invention, there is provided a compound of general formula

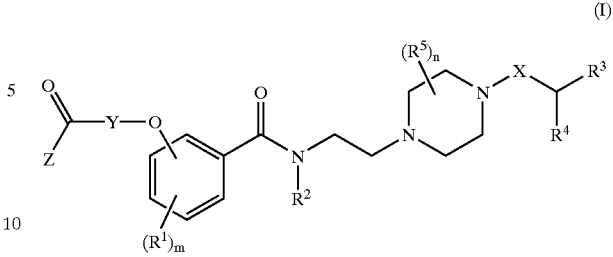

wherein:
each $R^1$ represents a substituent independently selected from halogen, C1 to 6 alkyl, C1 to 6 alkoxy, amino, nitro, cyano, $SO_2NH_2$, C1 to 6 haloalkyl, C1 to 6 haloalkoxy and C1 to 6 alkylsulphonyl;
m represents an integer 0 to 2;
$R^2$ represents hydrogen or C1 to 4 alkyl;
$R^3$ and $R^4$ independently represent hydrogen, C1 to 4 alkyl or phenyl; each phenyl group being optionally substituted by one or more substituents chosen independently from halogen, amino, nitro, cyano, C1 to 6 alkyl, C1 to 6 alkoxy, $SO_3H$, $SO_2NH_2$, C1 to 6 haloalkyl, C1 to 6 haloalkoxy and C1 to 6 alkylsulphonyl;
each $R^5$ independently represents hydrogen or C1 to 4 alkyl;
n represents an integer 0 to 4;
X represents a bond or C1 to 4 alkyl;
Y represents C1 to 4 alkyl;
Z represents OH or $NR^6R^7$;
  $R^6$ and $R^7$ independently represent hydrogen, C1 to 6 alkyl, C2 to 6 unsaturated alkyl; each alkyl group being optionally substituted by one or more substituents independently chosen from hydroxyl, C1 to 4 alkoxy, amino, $NR^8R^9$, 1-pyrrolidin-2-onyl and $CO_2R^{10}$;
  or the group $NR^6R^7$ together represents a 3 to 8 membered saturated or unsaturated azacyclic ring system optionally incorporating one or two further heteroatoms independently selected from N, O and S; said ring system being optionally further substituted by $CO_2R^{11}$, $COR^{12}$, $CONR^{13}R^{14}$ or C1 to 4 alkyl; said alkyl group itself being optionally further substituted by hydroxyl; and
  $R^8$, $R^9$, $R^{10}$, $R^{11}$, $R^{12}$, $R^{13}$ and $R^{14}$ independently represent hydrogen or C1 to 4 alkyl;
or a pharmaceutically acceptable salt or solvate thereof.

In one preferred embodiment, X represents a bond, $R^3$ represents optionally substituted phenyl and $R^4$ represents hydrogen.

Preferably $R^1$ represents halogen and m represents 1 or 2. More especially, $R^1$ represents chloro. Even more especially, $R^1$ represents chloro and m represents 1.

Preferably, Z represents $NR^6R^7$.
Preferably, each $R^5$ represents hydrogen.
Preferably, Y represents $CH_2$.

The term "C1 to 6 alkyl" referred to herein denotes a straight or branched chain alkyl group having from 1 to 6 carbon atoms and/or a cyclic alkyl group having from 3 to 6 carbon atoms. Examples of such groups include methyl, ethyl, n-propyl, i-propyl, n-butyl, i-butyl, t-butyl, cyclopentyl, methylcyclopentyl and cyclohexyl.

The term "C1 to 4 alkyl" is to be interpreted analogously.
The term "C2 to 6 unsaturated alkyl" referred to herein denotes a straight or branched chain alkyl group having from 2 to 6 carbon atoms and including one double bond or one triple bond or a cyclic alkyl group having from 3 to 6 carbon atoms and including one double bond. Examples of such groups include ethenyl, ethynyl, 1- and 2-propenyl, 1- and 2-propynyl, 2-methyl-2-propenyl, 2-butenyl, 2-butynyl, cyclopentenyl and cyclohexenyl.

The term "C1 to 6 alkoxy" referred to herein denotes an oxygen atom bonded to a straight or branched chain alkyl group having from 1 to 6 carbon atoms or an oxygen atom bonded to a cyclic alkyl group having from 3 to 6 carbon atoms.. Examples of such groups include methoxy, ethoxy, n-propoxy, i-propoxy, n-butoxy, i-butoxy, s-butoxy, t-butoxy, cyclopropyloxy and cyclohexyloxy.

The term "halogen" referred to herein denotes fluorine, chlorine, bromine and iodine.

The terms "C1 to 6 haloalkyl" (for example, chloromethyl, 2-fluoroethyl and trifluoromethyl) and "C1 to 6 haloalkoxy" (for example, trifluoromethoxy) are to be interpreted analogously.

Similarly, the term "C1 to 6 alkylsulphonyl" represents such groups as methylsulphonyl, t-butylsulphonyl and cyclohexylsulphonyl.

Examples of a "3 to 8 membered saturated or unsaturated azacyclic ring system optionally incorporating one or two further heteroatoms independently selected from N, O and S" include pyrrolidine, piperidine, morpholine, piperazine, pyrroline, pyrazoline, imidazolidine, tetrahydroazepine and perhydroazepine.

The present invention includes compounds of formula (I) in the form of salts, in particular acid addition salts. Suitable salts include those formed with both organic and inorganic acids. Such acid addition salts will normally be pharmaceutically acceptable although salts of non-pharmaceutically acceptable acids may be of utility in the preparation and purification of the compound in question. Thus, preferred salts include those formed from hydrochloric, hydrobromic, sulphuric, phosphoric, citric, tartaric, lactic, pyruvic, acetic, succinic, fumaric, maleic, methanesulphonic and benzenesulphonic acids.

Examples of particular compounds of the invention include:

4-chloro-2-[2-(dimethylamino)-2-oxoethoxy]-N-[2-(4-phenethyl-1-piperazinyl)ethyl]benzamide;
2-{5-chloro-2-[({2-[4-(3,4-dichlorobenzyl)-1-piperazinyl]ethyl}amino)carbonyl]phenoxy}acetic acid;
4-chloro-N-{2-[4-(3,4-dichlorobenzyl)-1-piperazinyl]ethyl}-2-[2-(dimethylamino)-2-oxoethoxy]benzamide;
4-chloro-N-{2-[4-(3,4-dichlorobenzyl)-1-piperazinyl]ethyl}-2-{2-[(2-hydroxy-1-methylethyl)amino]-2-oxoethoxy}benzamide;
4-chloro-N-{2-[4-(3,4-dichlorobenzyl)-1-piperazinyl]ethyl}-2-{2-[(2-hydroxy-1,1-dimethylethyl)amino]-2-oxoethoxy}benzamide;
4-chloro-N-{2-[4-(3,4-dichlorobenzyl)-1-piperazinyl]ethyl}-2-[2-(methylamino)-2-oxoethoxy]benzamide;
4-chloro-N-{2-[4-(3,4-dichlorobenzyl)-1-piperazinyl]ethyl}-2-[2-oxo-2-(1-pyrrolidinyl)ethoxy]benzamide;
2-(2-amino-2-oxoethoxy)-4-chloro-N-{2-[4-(3,4-dichlorobenzyl)-1-piperazinyl]ethyl}benzamide;
4-chloro-N-(2-{4-[1-(4-chlorophenyl)ethyl]-1-piperazinyl}ethyl)-2-[2-(dimethyalmino)-2-oxoethoxy]benzamide;
4-chloro-N-{2-[4-(3,4-dichlorobenzyl)-1-piperazinyl]ethyl}-2-[2-(diethylamino)-2-oxoethoxy]benzamide;
4-chloro-N-{2-[4-(3,4-dichlorobenzyl)-1-piperazinyl]ethyl}-2-{2-[[2-(dimethylamino)ethyl](methyl)amino]-2-oxoethoxy}benzamide;
2-[(2-{5-chloro-2-[({2-[4-(3,4-dichlorobenzyl)-1-piperazinyl]ethyl}amino)carbonyl]phenoxy}acetyl)amino]acetic acid;
4-chloro-N-{2-[4-(3,4-dichlorobenzyl)-1-piperazinyl]ethyl}-2-[2-(dimethylamino)-2-oxoethoxy]-N-methylbenzamide;
N-[2-(4-benzhydryl-1-piperazinyl)ethyl]-4-chloro-2-[2-(dimethylamino)-2-oxoethoxy]benzamide;
4-chloro-2-[2-(dimethylamino)-2-oxoethoxy]-N-{2-[4-(4-fluorobenzyl)-2,5-dimethyl-1-piperazinyl]ethyl}benzamide;
E-4-chloro-N-{2-[4-(3,4-dichlorobenzyl)-2,5-dimethyl-1-piperazinyl]ethyl}-2-[2-(dimethylamino)-2-oxoethoxy]benzamide;
4-chloro-N-{2-[4-(3,4-dichlorobenzyl)-1-piperazinyl]ethyl}-2-{2-[4-(2-hydroxyethyl)-1-piperazinyl]-2-oxoethoxy}benzamide;
4-chloro-N-{2-[4-(3,4-dichlorobenzyl)-1-piperazinyl]ethyl}-2-[2-(4-morpholinyl)-2-oxoethoxy]benzamide;
4-chloro-N-{2-[4-(3,4-dichlorobenzyl)-1-piperazinyl]ethyl}-2-{2-[(2-methoxyethyl)amino]-2-oxoethoxy}benzamide;
4-chloro-N-{2-[4-(3,4-dichlorobenzyl)-1-piperazinyl]ethyl}-2-{2-[3-(hydroxymethyl)-1-piperidinyl]-2-oxoethoxy}benzamide;
4-chloro-N-{2-[4-(3,4-dichlorobenzyl)-1-piperazinyl]ethyl}-2-{2-[(2-hydroxyethyl)(methyl)amino]-2-oxoethoxy}benzamide;
2-[2-(4-acetyl-1-piperazinyl)-2-oxoethoxy]-4-chloro-N-{2-[4-(3,4-dichlorobenzyl)-1-piperazinyl]ethyl}benzamide;
4-chloro-N-{2-[4-(3,4-dichlorobenzyl)-1-piperazinyl]ethyl}-2-{2-[ethyl(2-hydroxyethyl)amino]-2-oxoethoxy}benzamide;
4-chloro-N-{2-[4-(3,4-dichlorobenzyl)-1-piperazinyl]ethyl}-2-(2-oxo-2-{[3-(2-oxo-1-pyrrolidinyl)propyl]amino}ethoxy)benzamide;
ethyl 1-(2-{5-chloro-2-[({2-[4-(3,4-dichlorobenzyl)-1-piperazinyl]ethyl}amino)carbonyl]phenoxy}acetyl)-4-piperidinecarboxylate;
ethyl 1-(2-{5-chloro-2-[({2-[4-(3,4-dichlorobenzyl)-1-piperazinyl]ethyl}amino)carbonyl]phenoxy}acetyl)-3-piperidinecarboxylate;
methyl 2-[(2-{5-chloro-2-[({2-[4-(3,4-dichlorobenzyl)-1-piperazinyl]ethyl}amino)carbonyl]phenoxy}acetyl)amino]acetate;
4-chloro-N-{2-[4-(3,4-dichlorobenzyl)-1-piperazinyl]ethyl}-2-(2-{[1-(hydroxymethyl)cyclopentyl]amino}-2-oxoethoxy)benzamide;
4-chloro-N-{2-[4-(3,4-dichlorobenzyl)-1-piperazinyl]ethyl}-2-(2-{[2-(hydroxy-1-(hydroxymethyl)ethyl]amino}-2-oxoethoxy)benzamide;
1-(2-{5-chloro-2-[({2-[4-(3,4-dichlorobenzyl)-1-piperazinyl]ethyl}amino)carbonyl]phenoxy}acetyl)-2-pyrrolidinecarboxamide;
4-chloro-N-{2-[4-(3,4-dichlorobenzyl)-1-piperazinyl]ethyl}-2-{2-[4-(2-hydroxyethyl)-1-piperidinyl]-2-oxoethoxy}benzamide;
4-chloro-N-{2-[4-(3,4-dichlorobenzyl)-1-piperazinyl]ethyl}-2-[2-oxo-2-(2-propynylamino)ethoxy]benzamide;
4-chloro-N-{2-[4-(3,4-dichlorobenzyl)-1-piperazinyl]ethyl}-2-[2-(4-methyl-1,4-diazepan-1-yl)-2-oxoethoxy]benzamide;
4-chloro-N-{2-[4-(3,4-dichlorobenzyl)-1-piperazinyl]ethyl}-2-(2-{[1-(hydroxymethyl)propyl]amino}-2-oxoethoxy)benzamide;
4-chloro-N-{2-[4-(3,4-dichlorobenzyl)-1-piperazinyl]ethyl}-2-[2-oxo-2-(1-piperazinyl)ethoxy]benzamide;

N-[2-(4-benzyl-1-piperazinyl)ethyl]-4-chloro-2-[2-(dimethylamino)-2-oxoethoxy]benzamide;
4-chloro-2-[2-(dimethylamino)-2-oxoethoxy]-N-{2-[4-(4-fluorobenzyl)-1-piperazinyl]ethyl}benzamide;
4-chloro-2-[2-(dimethylamino)-2-oxoethoxy]-N-{2-[4-(4-methylbenzyl)-1-piperazinyl]ethyl}benzamide;
4-chloro-N-{2-[4-(4-chlorobenzyl)-1-piperazinyl]ethyl}-2-[2-(dimethylamino)-2-oxoethoxy]benzamide;
4-chloro-2-[2-(dimethylamino)-2-oxoethoxy]-N-{2-[4-(3,4-dimethylbenzyl)-1-piperazinyl]ethyl}benzamide;
4-chloro-N-{2-[4-(4-cyanobenzyl)-1-piperazinyl]ethyl}-2-[2-(dimethylamino)-2-oxoethoxy]benzamide;
4-chloro-N-{2-[4-(3-cyanobenzyl)-1-piperazinyl]ethyl}-2-[2-(dimethylamino)-2-oxoethoxy]benzamide;
4-chloro-N-{2-[4-(3-chlorobenzyl)-1-piperazinyl]ethyl}-2-[2-(dimethylamino)-2-oxoethoxy]benzamide;
4-chloro-N-{2-[4-(2,3-dichlorobenzyl)-1-piperazinyl]ethyl}-2-[2-(dimethylamino)-2-oxoethoxy]benzamide;
4-chloro-2-[2-(dimethylamino)-2-oxoethoxy]-N-{2-[4-(2,3,4-trifluorobenzyl)-1-piperazinyl]ethyl}benzamide;
4-chloro-2-[2-(dimethylamino)-2-oxoethoxy]-N-{2-[4-(2,4,5-trifluorobenzyl)-1-piperazinyl]ethyl}benzamide;
and pharmaceutically acceptable salts thereof.

The present invention further provides a process for the preparation of a compound of formula (1) which comprises:

(i) reacting a compound of general formula (II)

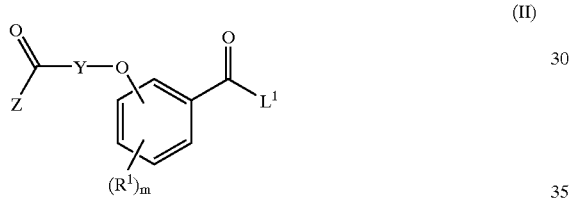

wherein $R^1$, m, Y and Z are as defined in formula (I) and $L^1$ represents a leaving group, with a compound of general formula (III)

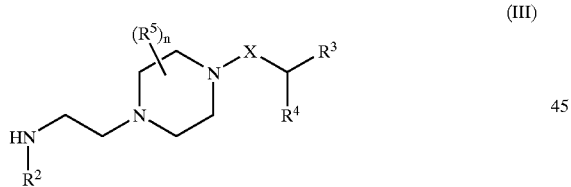

or an acid addition salt thereof,
wherein $R^2$, $R^3$, $R^4$, $R^5$, X and n are as defined in formula (I); or (ii) reacting a compound of general formula (IV)

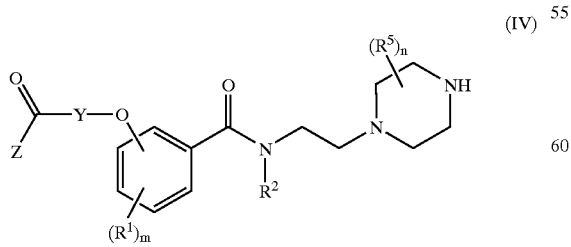

wherein $R^1$, $R^2$, $R^5$, Y, Z, m and n are as defined in formula (I), with a compound of general formula (V)

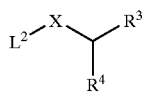

wherein $R^3$, $R^4$ and X are as defined in formula (I) and $L^2$ represents a leaving group; or (iii) when X represents $CH_2$, reacting a compound of general formula (IV)

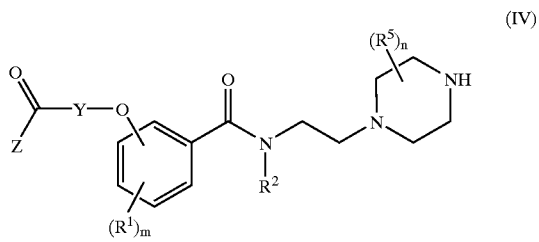

wherein $R^1$, $R^2$, $R^5$, Y, Z, m and n are as defined in formula (I), with a compound of general formula (VI)

wherein $R^3$ and $R^4$ are as defined in formula (I), using the process of reductive amination; or (iv) when Z represents $NR^6R^7$, reacting a compound of general formula (VII)

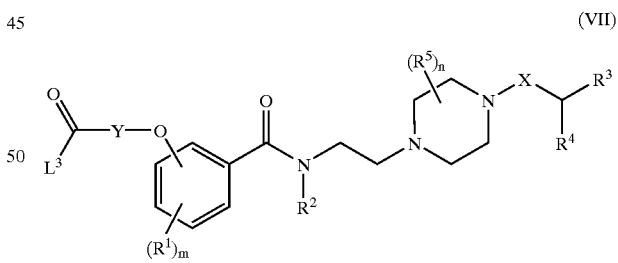

wherein $R^1$, $R^2$, $R^3$, $R^4$, $R^5$, X, Y, m and n are as defined in formula (I) and $L^3$ is a leaving group, with a compound of general formula (VII)

wherein $R^6$ and $R^7$ are as defined in formula (I); or (v) reacting a compound of general formula (IX)

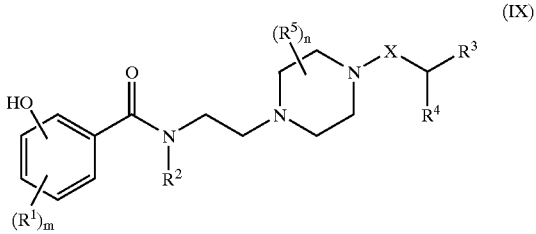

wherein $R^1$, $R^2$, $R^3$, $R^4$, $R^5$, X, m and n are as defined in formula (I), with a compound of formula (X)

wherein Y and Z are as defined in formula (I) and $L^4$ is a leaving group; or (vi) reacting a compound of general formula (XI)

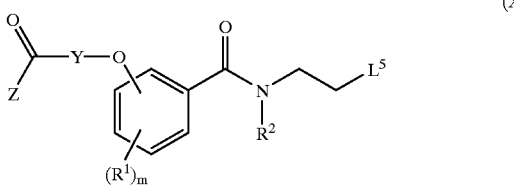

wherein $R^1$, $R^2$, Y, Z and m are as defined in formula (I) and $L^5$ is a leaving group, with a compound of formula (XII)

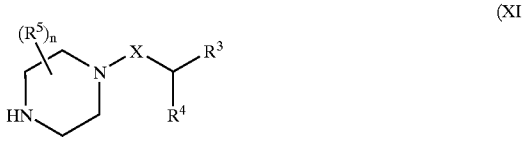

wherein $R^3$, $R^4$, $R^5$, X and n are as defined in formula (I); or (vii) preparing a compound of formula (I) wherein $R^2$ represents alkyl C1 to 4, by alkylation of a corresponding compound of formula (I) wherein $R^2$ represents hydrogen;

and optionally after (i), (ii), (iii), (iv), (v), (vi) or (vii) converting the compound of formula (I) to a further compound of formula (I) and/or forming a pharmaceutically acceptable salt or solvate of the compound of formula (I).

Salts of compounds of formula (I) may be formed by reacting the free base or another salt thereof, with one or more equivalents of the appropriate acid. The reaction may be carried out in a solvent in which the salt is insoluble, or in a solvent in which the salt is soluble, followed by subsequent removal of the solvent in vacuo or by freeze drying. Suitable solvents include, for example, water, dioxan, ethanol, 2-propanol, tetrahydrofuran or diethyl ether, or mixtures thereof. The reaction may also be carried out on an ion exchange resin.

In processes (i) and (iv) above, the reaction will take place on stirring a mixture of the reactants in a suitable organic solvent at a suitable temperature, generally between 0° C. and the boiling point of the solvent. The reaction time will depend inter alia on the solvent used, the reaction temperature and the nature of the leaving group. The reaction may be catalysed by the addition of a base; bases that may be used include organic amines (for example, triethylamine or pyridine) and alkali metal hydroxides, alkoxides, carbonates or hydrides. Suitable leaving groups, $L^1$ and $L^3$, include halogen (especially chlorine) and hydroxyl. When the leaving group is OH, the reaction between compounds of formulae (II) and (III), or between compounds of formulae (VII) and $HNR^6R^7$ may also be achieved using a suitable coupling agent such as CDI (1,1'-carbonyldiimidazole), DCC (1,3-dicyclohexylcarbodiimide) or HOBt (1-hydroxybenzotriazole).

In processes (ii) and (vi), the reaction is performed by treating an amine of general formula (IV) or (XII) with an electrophile of general formula (V) or (XI) respectively in an inert solvent. Suitable leaving groups $L^2$ and $L^5$ include sulfonate, trifluorosulfonate, tosylate, and halides selected from the group chloride, bromide or iodide. The reaction is generally performed in the presence of a base. This base can be either an excess of the amine nucleophile or can be an additive to the reaction mixture. Potential basic additives are metal carbonates, especially alkali metal carbonates such as cesium carbonate, metal oxides and hydroxides, and tertiary amine bases. Suitable organic solvents are those such as acetonitrile, dioxane, N,N-dimethylformamide, N-methyl-2-pyrrolidinone, tetrahydrofuran, dimethylsulfoxide, sulfolane and C1 to 4 alcohols. In a preferred embodiment, the leaving group is chloride.

In process (iii), the reductive amination reaction generally takes place under conditions which will be known to persons skilled in the art. For example, treatment of an aldehyde with an amine in the presence of a reducing agent in an inert solvent. Suitable reducing systems include catalytic hydrogenation or borane and derivatives thereof. A partial list of such reagents can be found in "Advanced Organic Chemistry", J. March (1985) $3^{rd}$ Edition on page 799.

In process (v) and (vii), the reaction will generally take place under similar conditions to those described above for processes (ii) and (vi).

Compounds of formula (IX) may be prepared by demethylation of a corresponding compound of formula (XIII)

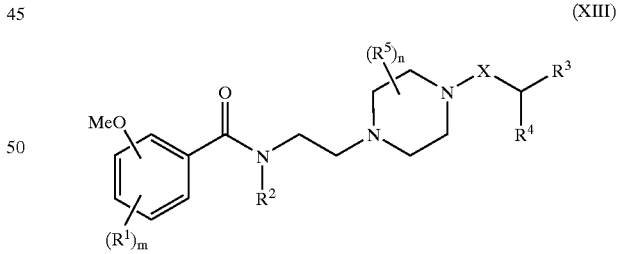

wherein $R^1$, $R^2$, $R^3$, $R^4$, $R^5$, X, m and n are as defined in formula (I), using, for example, boron tribromide.

In general, compounds of formulae (II), (IV), (VII), (IX), (XI) and (XIII) may be prepared using similar types of reactions to those described above for compounds of formula (I).

Novel intermediates of formulae (II), (IV), (VII), (IX), (XI) and (XIII) form another aspect of the invention.

Compounds of formulae (III), (V), (VI), (VIII), (X) and (XII) are either commercially available, or are known in the literature or may be prepared using methods which will be readily apparent to the man skilled in the art.

It will be appreciated by those skilled in the art that in the processes of the present invention certain functional groups such as hydroxyl or amino groups in the starting reagents or intermediate compounds may need to be protected by protecting groups. Thus, the preparation of the compounds of formula (I) may involve, at an appropriate stage, the addition and subsequent removal of one or more protecting groups.

The protection and deprotection of functional groups is described in 'Protective Groups in Organic Chemistry', edited by J. W. F. McOmie, Plenum Press (1973) and 'Protective Groups in Organic Synthesis', 2nd edition, T. W. Greene and P. G. M. Wuts, Wiley-Interscience (1991).

Certain compounds of formula (I) are capable of existing in stereoisomeric forms. It will be understood that the invention encompasses the use of all geometric and optical isomers of the compounds of formula (I) and mixtures thereof including racemates. The use of tautomers and mixtures thereof also form an aspect of the present invention.

The compounds of the invention and intermediates may be isolated from their reaction mixtures, and if necessary further purified, by using standard techniques.

The compounds of formula (I) have activity as pharmaceuticals, in particular as modulators of chemokine receptor activity. More particularly, the compounds have utility as modulators of the activity of chemokine receptors CCR1 and/or CCR3.

A further aspect of the invention involves the use of a compound of general formula (I) in the treatment of conditions or diseases in which modulation of chemokine receptor activity is beneficial.

Thus, compounds of general formula (I) may be used in the treatment of autoimmune, inflammatory, proliferative and hyperproliferative diseases and immunologically-mediated diseases including rejection of transplanted organs or tissues and Acquired Immunodeficiency Syndrome (AIDS).

Examples of these conditions include:

(1) (the respiratory tract) obstructive airways diseases including chronic obstructive pulmonary disease (COPD); asthma, such as bronchial, allergic, intrinsic, extrinsic and dust asthma, particularly chronic or inveterate asthma (e.g. late asthma and airways hyper-responsiveness); bronchitis; acute, allergic, atrophic rhinitis and chronic rhinitis including rhinitis caseosa, hypertrophic rhinitis, rhinitis purulenta, rhinitis sicca and rhinitis medicamentosa; membranous rhinitis including croupous, fibrinous and pseudomembranous rhinitis and scrofoulous rhinitis; seasonal rhinitis including rhinitis nervosa (hay fever) and vasomotor rhinitis; sarcoidosis, farmer's lung and related diseases, fibroid lung and idiopathic interstitial pneumonia;

(2) (bone and joints) rheumatoid arthritis, osteoarthritis, seronegative spondyloarthropathies (including ankylosing spondylitis, psoriatic arthritis and Reiter's disease), Behcet's disease, Sjogren's syndrome and systemic sclerosis;

(3) (skin) psoriasis, atopical dermatitis, contact dermatitis and other eczmatous dermitides, seborrhoetic dermatitis, *Lichen planus*, Pemphigus, bullous Pemphigus, *Epidermolysis bullosa*, urticaria, angiodermas, vasculitides, erythemas, cutaneous eosinophilias, uveitis, *Alopecia areata* and vernal conjunctivitis;

(4) (gastrointestinal tract) Coeliac disease, proctitis, eosinopilic gastro-enteritis, mastocytosis, Crohn's disease, inflammatory bowel disease, irritable bowel syndrome, ulcerative colitis, food-related allergies which have effects remote from the gut, e.g., migraine, rhinitis and eczema;

(5) (other tissues and systemic disease) multiple sclerosis, atherosclerosis, Acquired Immunodeficiency Syndrome (AIDS), lupus erythematosus, systemic lupus, erythematosus, Hashimoto's thyroiditis, myasthenia gravis, type I diabetes, nephrotic syndrome, eosinophilia fascitis, hyper IgE syndrome, lepromatous leprosy, sezary syndrome and idiopathic thrombocytopenia pupura; and (6) (allograft rejection) acute and chronic following, for example, transplantation of kidney, heart, liver, lung, bone marrow, skin and cornea; and chronic graft versus host disease.

Thus, the present invention provides a compound of formula (I), or a pharmaceutically-acceptable salt or solvate thereof, as hereinbefore defined for use in therapy.

In a further aspect, the present invention provides the use of a compound of formula (I), or a pharmaceutically acceptable salt or solvate thereof, as hereinbefore defined in the manufacture of a medicament for use in therapy.

In the context of the present specification, the term "therapy" also includes "prophylaxis" unless there are specific indications to the contrary. The terms "therapeutic" and "therapeutically" should be construed accordingly.

Prophylaxis is expected to be particularly relevant to the treatment of persons who have suffered a previous episode of, or are otherwise considered to be at increased risk of, the disease or condition in question. Persons at risk of developing a particular disease or condition generally include those having a family history of the disease or condition, or those who have been identified by genetic testing or screening to be particularly susceptible to developing the disease or condition.

The invention also provides a method of treating an inflammatory disease in a person suffering from, or at risk of, said disease, which comprises administering to the person a therapeutically effective amount of a compound of formula (I), or a pharmaceutically acceptable salt or solvate thereof, as hereinbefore defined.

For the above-mentioned therapeutic uses the dosage administered will, of course, vary with the compound employed, the mode of administration, the treatment desired and the disorder indicated.

The compounds of formula (I) and pharmaceutically acceptable salts and solvates thereof may be used on their own but will generally be administered in the form of a pharmaceutical composition in which the formula (I) compound/salt/solvate (active ingredient) is in association with a pharmaceutically acceptable adjuvant, diluent or carrier. Depending on the mode of administration, the pharmaceutical composition will preferably comprise from 0.05 to 99%w (per cent by weight), more preferably from 0.05 to 80%w, still more preferably from 0.10 to 70%w, and even more preferably from 0.10 to 50%w, of active ingredient, all percentages by weight being based on total composition.

The present invention also provides a pharmaceutical composition comprising a compound of formula (I), or a pharmaceutically acceptable salt or solvate thereof, as hereinbefore defined, in association with a pharmaceutically acceptable adjuvant, diluent or carrier.

The invention further provides a process for the preparation of a pharmaceutical composition of the invention which comprises mixing a compound of formula (I), or a pharmaceutically acceptable salt or solvate thereof, as hereinbefore defined, with a pharmaceutically acceptable adjuvant, diluent or carrier.

The pharmaceutical compositions may be administered topically (e.g. to the lung and/or airways or to the skin) in the form of solutions, suspensions, heptafluoroalkane aerosols and dry powder formulations; or systemically, e.g. by oral administration in the form of tablets, capsules, syrups, powders or granules, or by parenteral administration in the form of solutions or suspensions, or by subcutaneous administration or by rectal administration in the form of suppositories or transdermally.

The invention will now be further explained by reference to the following illustrative examples.

EXAMPLE 1

4-Chloro-2-[2-(dimethylamino)-2-oxoethoxy]-N-[2-(4-phenethyl-1-piperazinyl)ethyl]benzamide

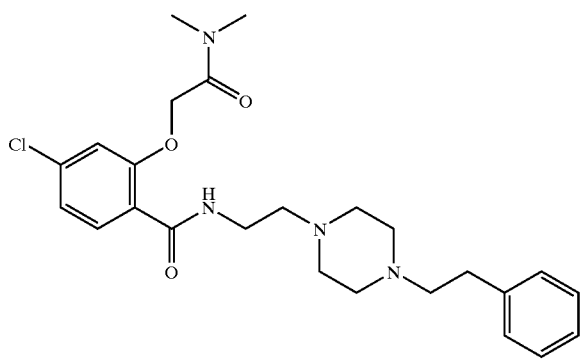

(a) 2-(Dimethylamino)-2-oxoethyl 4-chloro-2-[2-(dimethylamino)-2-oxoethoxy]benzoate A mixture of 4-chloro-2-hydroxybenzoic acid (5 g), cesium carbonate (17.5 g) and 2-chloro-N,N-dimethylacetamide (6.6 g) was stirred and heated at 70° C. for 3 hours. Water and ethyl acetate were added, the organic phase separated, dried and concentrated to give a gum which was purified by chromatography (ethyl acetate:methanol 9:1) to give the product as a solid (8.0 g), m.p. 140–141° C.

MS: APCI(+ve) 343(M+H).

(b) 4-Chloro-2-[2-(dimethylamino)-2-oxoethoxy] benzoic acid

The product from step (a) (1.0 g) was dissolved in a 2:1 water:methanol mixture (15 ml) and lithium hydroxide monohydrate added. After 2 hours 2M aqueous hydrochloric acid and ethyl acetate were added, the organic phase separated, dried and concentrated to give the product as a solid (1.2 g), m.p. 141–142° C.

MS: APCI(+ve) 258(M+H).

(c) tert-Butyl 4-[2-({4-chloro-2-[2-(dimethylamino)-2-oxoethoxy]benzoyl}amino)ethyl]-1-piperazinecarboxylate The product from step (b) (0.7 g) and 1,1'-carbonyldiimidazole (0.62 g) were dissolved in N,N-dimethylformamide (10 ml) and stirred at room temperature for 1 hour. tert-Butyl 4-(2-aminoethyl)-1-piperazinecarboxylate (2.73 g) was added, the solution stirred for 16 hours and then evaporated to leave a gum. Dichloromethane and sodium bicarbonate solution were added, the organic phase was separated, dried and concentrated to a gum which was purified by chromatography (ethyl acetate:triethylamine, 10:1) to give the product as a solid (0.62 g), m.p. 139–140° C.

MS: ESI: 469.22 (M+H).

(d) 4-Chloro-2-[2-(dimethylamino)-2-oxoethoxy]-N-[2-(1-piperazinyl)ethyl]benzamide trifluoroacetate The product of step (c) (0.55 g) was dissolved in dichloromethane (15 ml) and trifluoroacetic acid (3 ml) added. After 1 hour the solvent was evaporated and the product obtained as a solid (0.9 g), m.p. 120–122° C.

MS: ESI: 369.16 (M+H).

(e) 4-Chloro-2-[2-(dimethylamino)-2-oxoethoxy]-N-[2-(4-phenethyl-1-piperazinyl)ethyl]benzamide The product from step (d) (0.1 g) was dissolved in methanol (3 ml) and triethylamine (2 ml) added. The solvent was removed, the residue dissolved in N,N-dimethylformamide (2 ml) and phenylacetaldehyde (0.041 g) added followed by sodium triacetoxyborohydride (0.1 g). After 2 hours the solvent was removed to give a gum which was purified by chromatography (ethyl acetate:methanol:triethylamine, 85:5:10) to give the product as a solid (0.7 g), m.p. 159–160° C.

MS: ESI: 473.33 (M+H).

$^1$H NMR (d$_6$-DMSO) 9.1–9.2 (m, 1H), 9.89 (d, 1H), 7.37 (m, 1H), 7.1–7.3 (m, 6H), 5.1 (s, 2H), 3.35–3.5 (m, 2H), 2.99 (s, 3H), 2.89 (s, 3H), 2.7–2.8 (m, 2H), 2.3–2.5 (m, 10H).

EXAMPLE 2

2-{5-Chloro-2-[({2-[4-(3,4-dichlorobenzyl)-1-piperazinyl]ethyl}amino)carbonyl]phenoxy}acetic acid

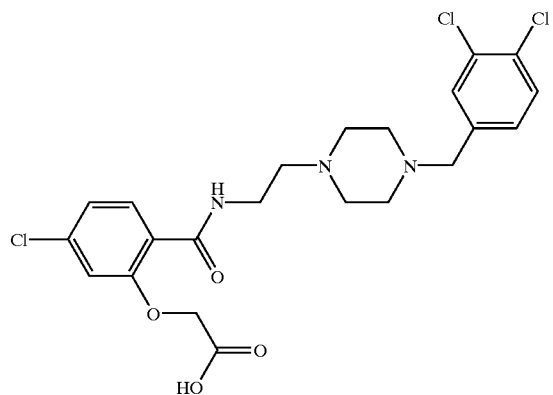

(a) 4-Chloro-2-methoxy-N-[2-(1-piperazinyl)ethyl] benzamide trifluoroacetate

A solution of 4-chloro-2-methoxybenzoyl chloride (2.1 g), tert-butyl 4-(2-aminoethyl)-1-piperazinecarboxylate (3.0 g) and triethylamine (2.6 ml) in dichloromethane (100 ml) was stirred at room temperature for 72 hours. The solution was washed with brine, dried and treated with trifluoroacetic acid. After 16 hours the solution was concentrated and the residue triturated under ether to give the product as an oil (4.1 g).

M.S. APCI(+ve) 298/300 (M+H).

(b) 4-Chloro-N-{2-[4-(3,4-dichlorobenzyl)-1-piperazinyl]ethyl}-2-methoxybenzamide dihydrochloride A solution of the product of step (a) (4.0 g), 3,4-dichlorobenzylchloride (1.9 ml) and triethylamine (9.0 ml)

in N,N-dimethylformamide (20 ml) was stirred at room temperature. The solvent was removed and the residue purified by chromatography (dichloromethane:methanol, 1:0 to 4:1) to give an oil, which was treated with 1.0M ethereal hydrogen chloride to give the product as a solid (3.1 g), m.p. 240–41° C.

MS: APCI(+ve) 456(M+H).

$^1$H NMR (CDCl$_3$) 8.23 (t,1H), 8.16 (d,1H), 7.44 (d,1H), 7.37 (d,1H), 7.17 (d,1H), 7.07 (dd,1H), 6.96 (d,1H), 3.96 (s,3H), 3.56 (q,2H), 3.48 (s,2H), 2.4–2.6 (t+m,1–H).

(c) 4-Chloro-N-{2-[4-(3,4-dichlorobenzyl)-1-piperazinyl]ethyl}-2-hydroxybenzamide A solution of the product of step (b) (3 g) in dichloromethane (50 ml) was cooled to −78° C. and a 1.0M solution of boron tribromide in dichloromethane (8.5 ml) added. After 1 hour the solution was allowed to warm to room temperature. After 3 hours, methanol (6 ml) was added and the solution concentrated. This process was repeated, the residue dissolved in methanol, treated with concentrated hydrochloric acid and stirred at room temperature for 3 hours. The solution was concentrated, sodium bicarbonate solution and ethyl acetate were added, the organic phase separated, dried and concentrated to a gum which was purified by chromatography (dichloromethane:methanol, 97:3) to give the product as a solid (2.0 g), m.p. 238–240° C.

MS: APCI(+ve) 442/444 (M+H).

$^1$H NMR (d$_6$-DMSO) 12.27 (s,1H), 9.10 (t, 1H), 7.96 (d, 1H), 7.82 (m, 1H), 7.72 (dd, 1H), 7.50 (m, 1H), 7.44 (dd, 1H), 7.00 (d, 1H), 3.2–3.97 (m,1 4H).

(d) Ethyl (2-{5-chloro-2-[({2-[4-(3,4-dichlorobenzyl)-1-piperazinyl]ethyl}amino)carbonyl]phenoxy}acetic acid hydrochloride A mixture of the product of step (c) (1.0 g), ethyl 2-bromoacetate (0.42 g) and cesium carbonate (0.81 g) was stirred and heated at 70° C. for 3 hours and then cooled. Water and ether were added, the organic phase was separated, washed with water and dried. Evaporation gave an oil which was treated with 1.0M ethereal hydrogen chloride solution to give a solid which was recrystallised from ethyl acetate to give the product as a solid which was used directly in the next step without further purification.

(e) (2-{5-Chloro-2-[({2-[4-(3,4-dichlorobenzyl)-1-piperazinyl]ethyl}amino)carbonyl]phenoxy}acetic acid The product from step (d) (0.9 g) was dissolved in a 1:1 methanol:water mixture (40 ml), lithium hydroxide monohydrate (0.25 g) was added and the solution stirred at room temperature for 3 hours. Evaporation gave a gum which was treated with aqueous hydrochloric acid to pH 6 and ethyl acetate added. The organic phase was separated, dried and evaporated to give a solid which was purified by chromatography (dichloromethane:methanol, 4:1) to give the product as a solid (0.31 g), m.p. 118–20° C.

MS: ESI 500.09(M+H).

$^1$H NMR (d$_6$-DMSO) 9.37 (t, 1H), 7.85 (d, 1H), 7.57 (d, 1H), 7.55 (d, 1H), 7.31 (dd, 1H), 7.26 (d, 1H), 7.14 (dd, 1H), 4.73 (s, 2H), 3.50 (m, 4H), 2.80 (m, 6H), 2.50 (m, 4H).

EXAMPLE 3

4-Chloro-N-{2-[4-(3,4-dichlorobenzyl)-1-piperazinyl]ethyl}-2-[2-(dimethylamino)-2-oxoethoxy]benzamide dihydrochloride

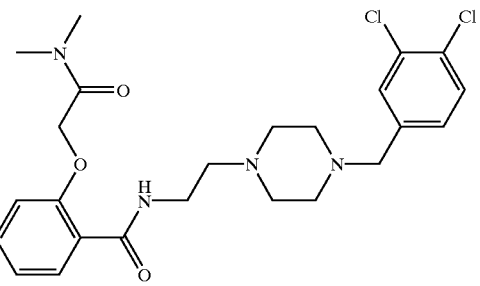

A solution of the product of Example 2(c) (0.6 g), cesium carbonate (0.89 g) and 2-chloro-N,N-dimethylacetamide (0.25 g) in N,N-dimethylformamide was heated at 70° C. for 5 hours. The solution was cooled, water and ether were added, the organic phase was separated, dried and concentrated to a gum which was purified by chromatography (dichloromethane:methanol, 20:1) to give an oil. Treatment with 1.0M ethereal hydrogen chloride solution gave the product as a solid (0.42 g), m.p. 162–63° C.

MS: ESI 527.13(M+H).

$^1$H NMR (d$_6$-DMSO) 9.15 (t, 1H), 7.87 (d, 1H), 7.59 (d, 1H), 7.53 (d, 1H), 7.37 (d, 1H), 7.28 (dd, 1H), 7.14 (dd, 1H), 5.01 (s, 2H), 3.42 (s, 2H), 3.40 (q, 2H), 3.01 (s, 3H), 2.84 (s, 3H), 2.3–2.5 (b, 10H).

EXAMPLE 4

4-Chloro-N-{2-[4-(3,4-dichlorobenzyl)-1-piperazinyl]ethyl}-2-{2-[(2-hydroxy-1-methylethyl)amino]-2-oxoethoxy}benzamide

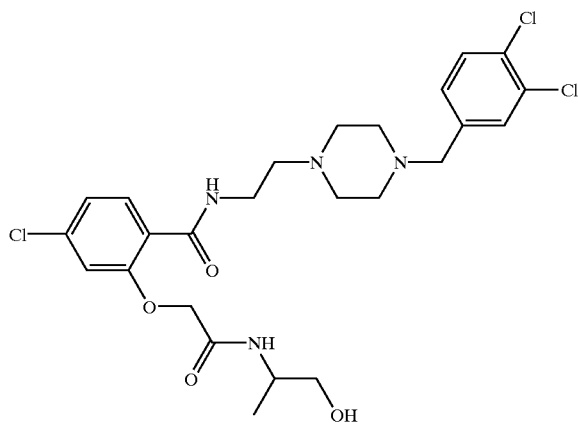

The product of Example 2 (0.3 g) was dissolved in N,N-dimethylformamide (3 ml). 1,1'-Carbonyldiimidazole (0.1 g) and 2-amino-1-propanol (5 molar equivalents) were added, the solution heated at 60° C. for 1.5 hours and cooled. Water and ether were added, the organic phase separated and concentrated to a gum which was purified by chromatography (dichloromethane:methanol, 9:1) to give the product as a solid (0.15 g), m.p. 115–116° C.

MS: APCI(+ve) 557/559 (M+H).

$^1$H NMR (d$_6$-DMSO) 8.63 (t, 1H), 8.07 (d, 1H), 7.75 (d, 1H), 7.56 (d, 1H), 7.30 (dd, 1H), 7.17 (dd, 1H), 4.78 (m,

3H), 3.84 (m,1 H), 3.42 (s, 2H), 3.3–3.4 (m, 6H), 2.4–2.5 (m, 8H), 1.04 (d. 3H).

EXAMPLE 5

4-Chloro-N-{2-[4-(3,4-dichlorobenzyl)-1-piperazinyl]ethyl}-2-{2[(2-hydroxy-1,1-dimethylethyl)amino]-2-oxoethoxy}benzamide

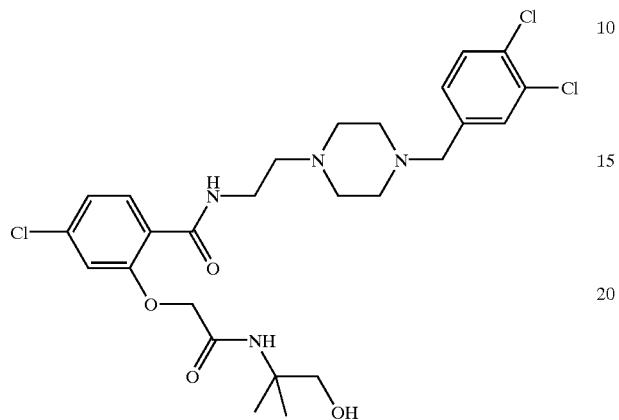

The title compound was prepared by the method of Example 4 using 2-amino-2-methyl-1-propanol to give the product as a solid, m.p. 77–78° C.

MS: APCI(+ve) 571/573 (M+H).

$^1$H NMR (d$_6$-DMSO) 8.65 (t, 1H), 7.73 (d, 1H), 7.66(s, 1H), 7.57 (d, 1H), 7.53 (d,1 H), 7.29 (dd, 1H), 7.12 (s+d, 2H), 4.82 (t, 1H), 4.66 (s, 2H), 3.38–3.45 (m, 8H), 2.37–2.47 (m, 8H), 1.21 (s, 6H).

EXAMPLE 6

4-Chloro-N-{2-[4-(3,4-dichlorobenzyl)-1-piperazinyl]ethyl}-2-[2-(methylamino)-2-oxoethoxy]benzamide

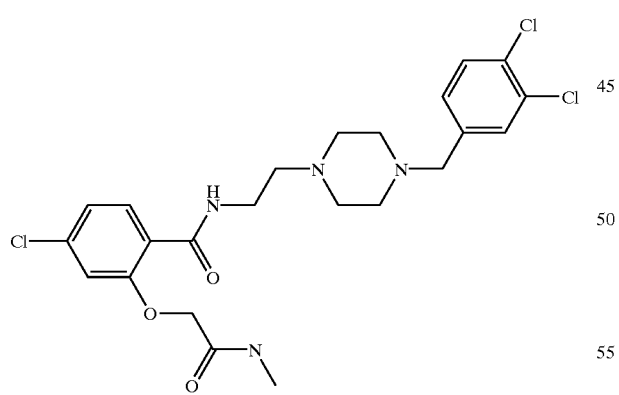

The title compound was prepared by the method of Example 4 using methylamine to give the product as a solid, m.p. 137–138° C.

MS: APCI(+ve) 513/515 (M+H).

$^1$H NMR (d$_6$-DMSO) 8.58 t, 1H), 8.21 (d, 1H), 7.73 (d, 1H), 7.58 (d, 1H), 7.53 (d, 1H), 7.30 (dd, 1H), 7.19 (d, H), 7.15 (dd, 1H), 4.74 (s, 2H), 3.39 (m, 2H), 3.32 (m, 4H), 2.67 (d, 3H), 2.4–2.5 (m, 8H).

EXAMPLE 7

4-Chloro-N-{2-[4-(3,4-dichlorobenzyl)-1-piperazinyl]ethyl}-2-[2-oxo-2-(1-pyrrolidinyl)ethoxy]benzamide

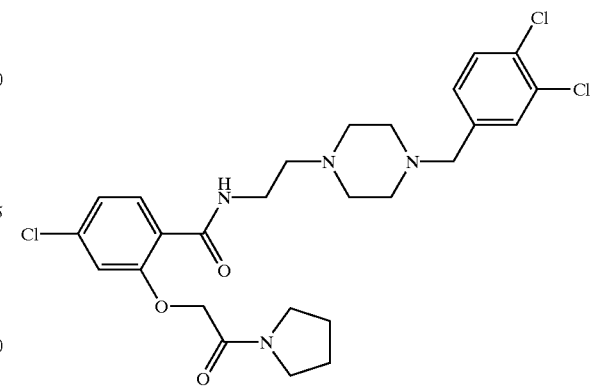

The title compound was prepared by the method of Example 4 using pyrrolidine to give the product as a solid, m.p. 157–158° C.

MS: APCI(+ve) 553/555 (M+H).

$^1$H NMR (d$_6$-DMSO) 9.11 (t, 1H), 7.85 (d, 1H), 7.58 (d, 1H), 7.52 (d, 1H), 7.36 (d, 1H), 7.29 (dd, 1H), 7.14 (dd, 1H), 5.02 (s, 2H), 3.3–3.5 (m, 10H), 2.3–2.5 (m, 8H), 1.95 (m, 2H), 1.88 (m, 2H).

EXAMPLE 8

2-(2-Amino-2-oxoethoxy)-4-chloro-N-{2-[4-(3,4-dichlorobenzyl)-1-piperazinyl]ethyl}benzamide

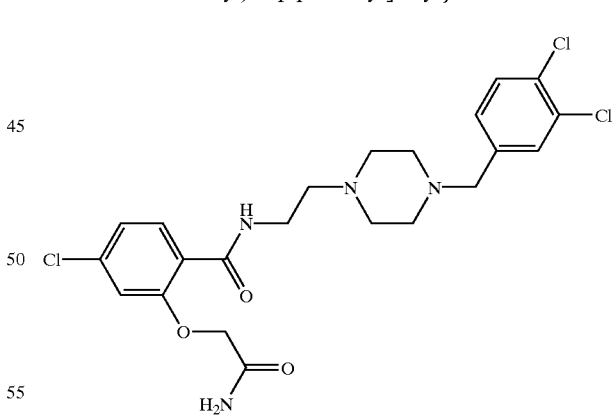

The title compound was prepared by the method of Example 4 using ammonia to give the product as a solid, m.p. 120–122° C.

MS: APCI(+ve) 499/501 (M+H).

$^1$H NMR (d$_6$-DMSO) 8.63 (t, 1H), 7.71 (d+s, 2H), 7.56 (d, 1H), 7.53 (d, H), 7.47 (s, 1H), 7.30 (dd, 1H), 7.17 (m, 2H), 4.70 (s, 2H), 3.38 (m, 2H), 3.31 (s+m, 4H), 2.4–2.5 (m, 8H).

EXAMPLE 9

4-Chloro-N-(2-{4-[1-(4-chlorophenyl)ethyl]-1-piperazinyl}ethyl)-2-[2-(dimethylamino)-2-oxoethoxy]benzamide hydrochloride

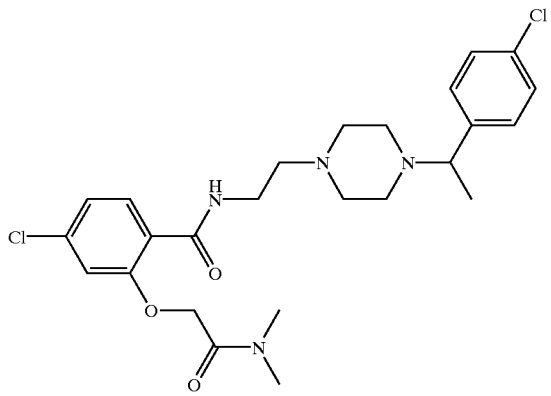

The product of Example 1(d) (0.3 g), α-methyl-4-chlorobenzyl chloride (0.09 g) and cesium carbonate (0.5 g) were dissolved in N,N-dimethylformamide and stirred and heated at 60° C. for 40 hours. Water and ether were added, the organic phase separated, dried and concentrated. The residue was purified by chromatography (dichloromethane:methanol, 93:7) to give an oil which was treated with 1.0M ethereal hydrogen chloride solution to give the product as a solid (0.1 g), m.p. 216–217° C.

MS: ESI 507.19 (M+H).

$^1$H NMR (d$_6$-DMSO) 7.92(d, 1H), 7.56–7.71 (m, 5H), 7.40 (d, 1H), 7.16 (dd,1 H), (dd,1 H), 5.10 (s, 2H), 4.49 (m, 1H), 4.1–4.25 (m, 4H), 3.70 (m, 4H), 3.30 (m, 4H), 2.99 (s, 3H), 2.88 (s, 3H), 1.63 (d, 3H).

EXAMPLE 10

4-Chloro-N-{2-[4-(3,4-dichlorobenzyl)-1-piperazinyl]ethyl}-2-[2-(dimethylamino)-2-oxoethoxy]benzamide dihydrochloride

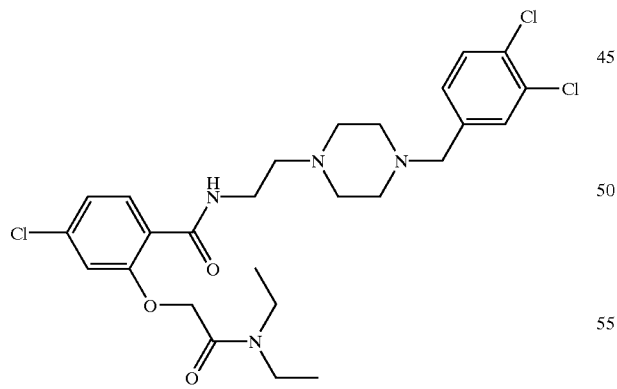

The title compound was prepared by the method of Example 4 using diethylamine to give an oil. Treatment with 1.0M ethereal hydrogen chloride solution gave the product as a solid, m.p. 185–188° C.

MS: ESI 557.17(M+H).

$^1$H NMR (d$_6$-DMSO) 7.96 (d, 1H), 7.60 (m, 4H), 7.45 (d, 1H), 7.19 (dd, 1H), 5.08 (s, 2H), 3.0–3.6 (m, 14H), 1.25 (m, 4H), 1.16 (t, 3H), 1.05 (t, 3H).

EXAMPLE 11

4-Chloro-N-{2-[4-(3,4-dichlorobenzyl)-1-piperazinyl]ethyl}-2-{2-[[2-(dimethylamino)ethyl](methyl)amino]-2-oxoethoxy}benzamide trihydrochgoride

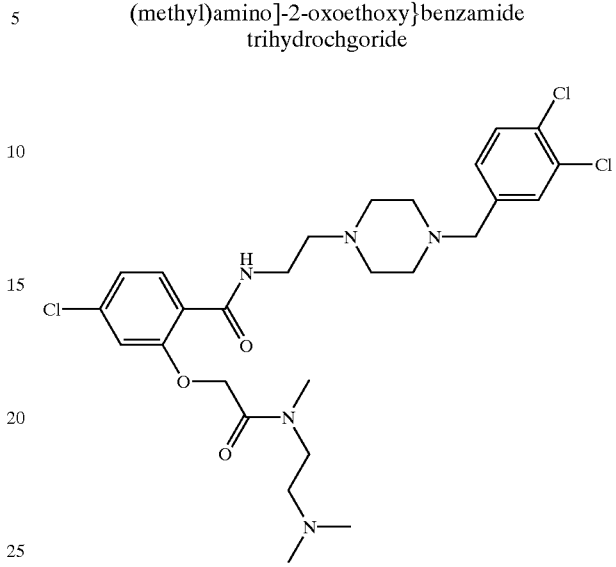

The title compound was prepared by the method of Example 4 using N,N,N-trimethylethylenediamine to give an oil. Treatment with 1.0M ethereal hydrogen chloride solution gave the product as a solid, m.p. 220–222° C.

MS: ESI 584.19 (M+H).

$^1$H NMR (d$_6$-DMSO) 9.38 (t, 1H), 7.91 (d, 2H), 7.71 (d, 1H), 7.59 (b, 1H), 7.46 (d, 1H), 7.16 (dd, 1H), 5.14 (s, 2H), 3.72 (m, 6H), 3.3–3.45 (m, 1OH), 3.02 (s, 3H), 2.80 (m, 8H).

EXAMPLE 12

2-[(2-{5-Chloro-2-[({2-[4-(3,4-dichlorobenzyl)-1-piperazinyl]ethyl}amino)carbonyl]phenoxy}acetyl)amino]acetic acid

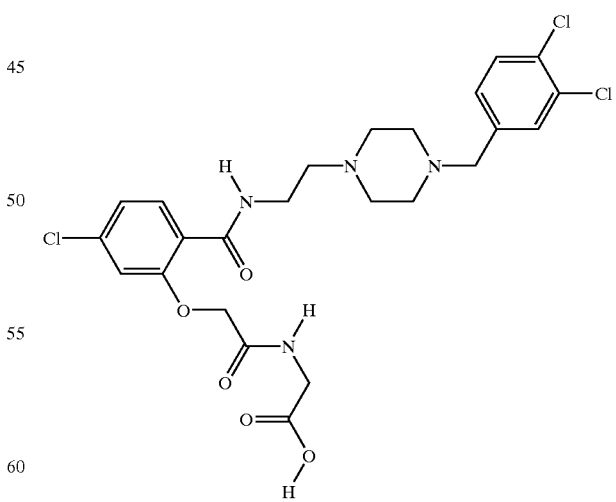

The title compound was prepared by the method of Example 4 using tert-butylglycine followed by addition of formic acid gave the product as a solid, m.p. 214–216° C.

MS: ESI 557.11 (M+H).

$^1$H NMR (d$_6$-DMSO) 8.56 (m, 2H), 7.76 (d, 1H), 7.59 (d, 1H), 7.53 (d, 1H), 7.30(dd, 1H), 7.19 (d, 1H), 7.15 (dd, 1H), 4.80 (s, 2H), 3.82 (d, 2H), 3.46 (s, 2H), 3.40 (m, 2H), 2.51 (m, 6H), 2.35 (m, 4H).

EXAMPLE 13

4-Chloro-N-{2-[4-(3,4-dichlorobenzyl)-1-piperazinyl]ethyl}-2-[2-dimethylamino)-2-oxoethoxy]-N-methylbenzamide trihydrochloride

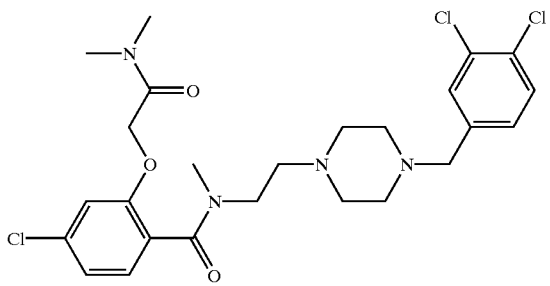

The product of Example 3 (0.1 g) was dissolved in N,N-dimethylformamide (5 ml) and sodium hydride (60% dispersion in mineral oil) (0.008 g) added. After 30 minutes methyl iodide (0.027 g) was added and the solution left at room temperature for 3 hours. Water and ether were added, the organic phase separated, dried and concentrated to give an oil. Purification by chromatography (dichloromethane:methanol, 97:3) gave an oil which was treated with 1.0M ethereal hydrogen chloride solution to give the product as a solid (0.02 g), m.p. 252–253° C.

MS: ESI 541.15 (M+H).

$^1$H NMR (d$_6$-DMSO) 7.81 (b, 1H), 7.62 (b, 1H), 7.51 (b, 1H), 7.27 (b, 1H), 7.09 (b, 2H), 4.89 (b, 2H), 4.02 (b, 8H), 2.86–3.42 (b, 15H).

EXAMPLE 14

N-[2-(4-Benzhydryl-1-piperazinyl)ethyl]-4-chloro-2-[2-(dimethylamino)-2-oxoethoxy]benzamide trihydrochloride

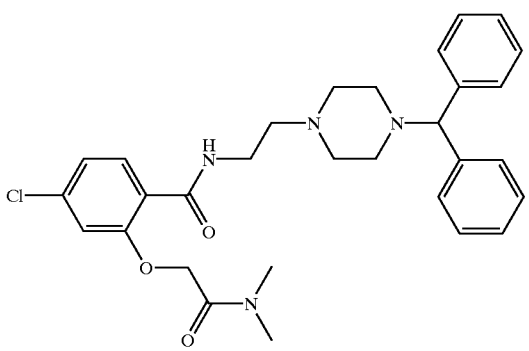

The product from Example 1(d) (0.1 g) was dissolved in N,N-dimethylformamide (5 ml), bromodiphenyl methane (0.046 g) and triethylamine (0.070 g) were added. After 16 hours at room temperature, water and ether were added, the organic phase was separated, dried and concentrated to an leave an oil.

The oil was dissolved in methanol, 1.0M ethereal hydrogen chloride solution was added and the solvent removed to give a solid which was triturated under ether to give the product as a solid (0.08 g), m.p. 228–229° C.

MS: APCI (+ve) 535(M+H).

$^1$H NMR (d$_6$-DMSO) 9.53 (t, 1H), 7.93 (d, H), 7.24–7.45 (m, 11H), 7.17 (dd, 1H), 5.10 (s, 2H), 3.93 (m, 6H), 3.71 (m, 2H), 3.57 (m, 2H), 3.34 (m, 2H),3.19 (m, 1H), 2.98 (s, 3H), 2.82 (s, 3H).

EXAMPLE 15

4-Chloro-2-[2-(dimethylamino)-2-oxoethoxyl-N-{2-[4-(4-fluorobenzyl)-2,5-dimethyl-1-piperazinyl]ethyl}benzamide dihydrochloride

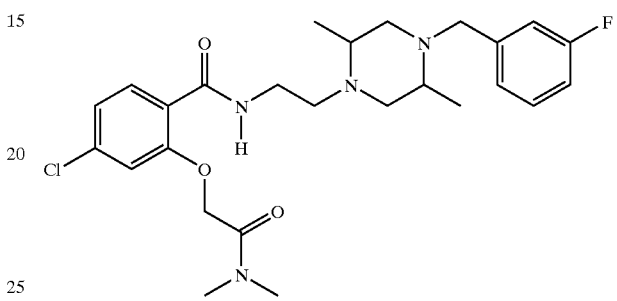

(a) E-1-(4-Fluorobenzyl)-2,5-dimethylpiperazine

E-2,5-Dimethylpiperazine and triethylamine (6 ml) were dissolved in dichloromethane (150 ml), 4-fluorobenzylbromide (5.34 ml) was added over 10 minutes and the solution stirred at room temperature for 20 hours. Water was added and the organic phase separated, dried and concentrated to an oil. Purification by chromatography (dichloromethane:ethyl acetate, 9:1 followed by dichloromethane:methanol, 9:1) gave the product as a solid (3.0 g).

MS: ESI (+ve) 223.16(M+H).

$^1$H NMR (CDCl$_3$) 7.29–7.24 (m, 2H), 7.05–6.9 (m, 2H), 4.05 (d, 1H), 3.05 (d, 1H), 3.05–2.5 (m, 5H), 2.2 (m, 1H), 1.6 (t,1H), 1.45 (bs, 1H), 1.07 (d, 3H), 0.95 (d, 3H).

(b) E-2-[4-(4-Fluorobenzyl)-2,5-dimethyl-1-piperazinyl]ethylamine

The product of step (a) (0.71 g), tert-butyl 2-bromoethylcarbamate (0.77 g) and triethylamine (0.71 ml) were dissolved in N,N-dimethylformamide (10 ml) and the solution stirred at room temperature for 5 days. Ethyl acetate and water were added, the organic phase was separated and concentrated to an oil which was purified by chromatography (ethyl acetate) to give an oil which was dissolved in dichloromethane. Trifluoroacetic acid (5 ml) was added and the solution stirred at room temperature for 20 hours. The solvent was evaporated to leave a solid which was used directly in the next step without further purification.

(c) E-4-Chloro-2-[2-(dimethylamino)-2-oxoethoxy]-N-{2-[4-(4-fluorobenzyl)-2,5-dimethyl-1-piperazinyl]ethyl}benzamide dihydrochloride The product of Example 1(b) (0.127 g) was dissolved in N,N-dimethylformamide (10 ml) and 1,1'-carbonyldiimidazole (0.08 g) added. After 1 hour the product of step (b) (0.3 g) was added and the solution stirred at room temperature for 20 hours. Water and ethyl acetate were added, the organic phase was separated, dried and concentrated to leave an oil. Purification by chromatography (dichloromethane:methanol, 9:1) gave an oil which was treated with 1.0M ethereal hydrogen chloride solution to give the product as a solid (0.13 g), m.p. 207–208° C.

MS: ESI 505.23(M+H).

$^1$H NMR (d$_6$-DMSO) 7.92 (d, 1H), 7.8–7.5 (m, 2H), 7.4 (d, 1H), 7.35–7.1 (m, 3H), 5.13 (s, 2H), 3.8 (bm, 12H), 3.0 (s, 3H), 2.9 (s, 3H), 1.6–1.2 (m, 6H).

EXAMPLE 16

E-4-Chloro-N-{2-[4-(3,4-dichlorobenzyl)-2,5-dimethyl-1-piperazinyl]ethyl}-2-[2-(dimethylamino)-2-oxoethoxy]benzamide dihydrochloride

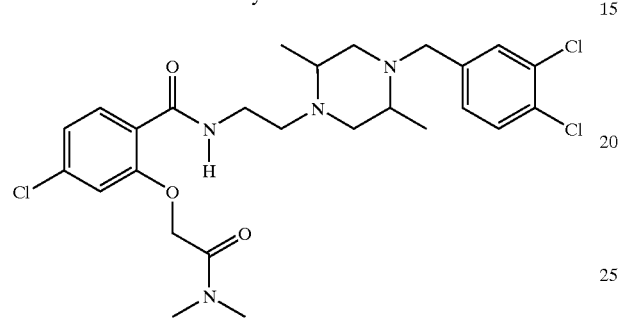

The title compound was prepared by the method of Example 15, using 3,4-dichlorobenzyl chloride in step (a), to give the product as a solid (0.01 g), m.p. 220–221° C.

MS: ESI(+ve) 555.16(M+H).

EXAMPLE 17

4-Chloro-N-{2-(3,4-dichlorobenzyl)-1-piperazinyl]ethyl}2-{2-[4(2-hydroxyethyl)-1-piperazinyl]-2-oxoethoxy}benzamide

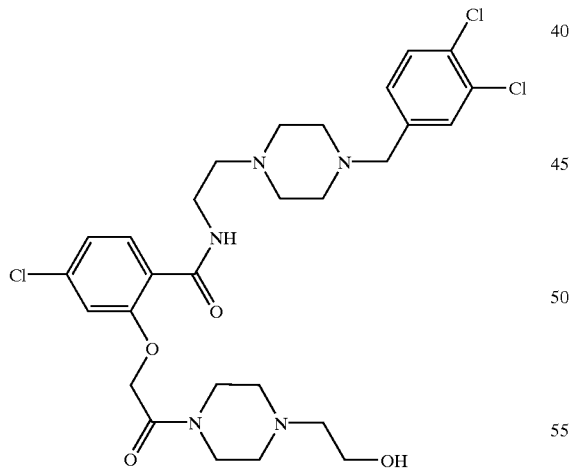

The product of Example 2 was dissolved in N,N-dimethylformamide and 1,1'-carbonyldiimidazole added. After 1 hour N-(2-hydroxyethyl)piperazine was added. The solution was left at room temperature for 24 hours and the solvent evaporated to give the product as an oil.

M.S. APCI (+ve) Base Peak 612.

Using the method of Example 17 together with the appropriate amine, the compounds of Examples 18 to 35 were prepared.

EXAMPLE 18

4-Chloro-N-{2-[4-(3,4-dichlorobenzyl)-1-piperazinyl]ethyl}-2-[2-(4-morpholinyl)-2-oxoethoxy]benzamide

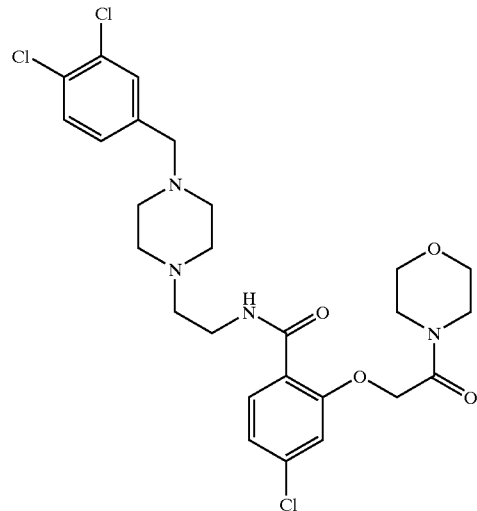

M.S. APCI (+ve) Base Peak 569.

EXAMPLE 19

4-Chloro-N-{2-[4-(3,4-dichlorobenzyl)-1-piperazinyl]ethyl}-2-{2-[(2-methoxyethyl)amino]-2-oxoethoxy}benzamide

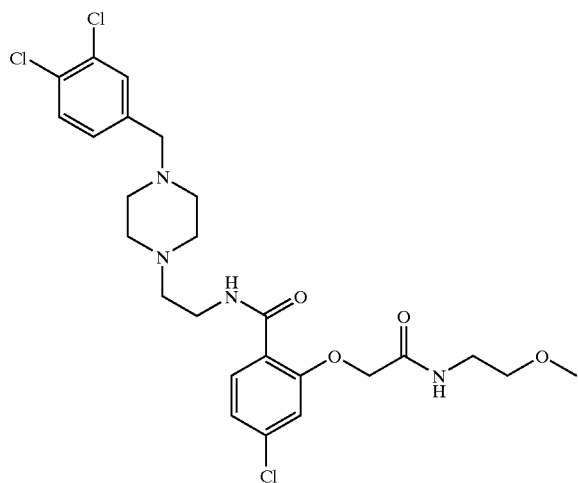

M.S. APCI (+ve) Base Peak 557.

EXAMPLE 20

4-Chloro-N-{2-[4-(3,4-dichlorobenzyl)-1-piperazinyl]ethyl}-2-{2-[3-(hydroxymethyl)-1-piperidinyl]-2-oxoethoxy}benzamide

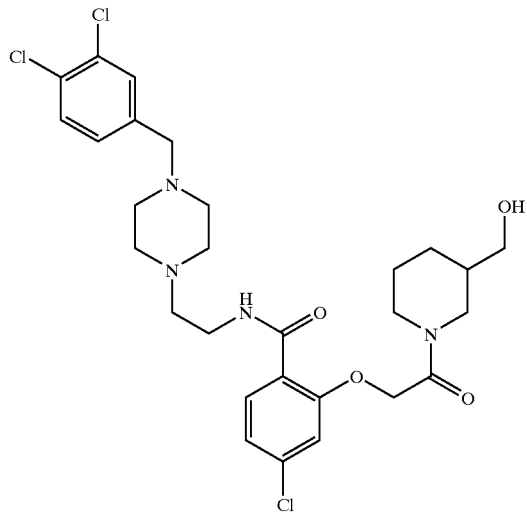

M.S. APCI (+ve) Base Peak 596.

EXAMPLE 21

4-Chloro-N-{2-[4-(3,4-dichlorobenzyl)-1-piperazinyl]ethyl}-2-{2-[(2-hydroxyethyl)(methyl)amino]-2-oxoethoxy}benzamide

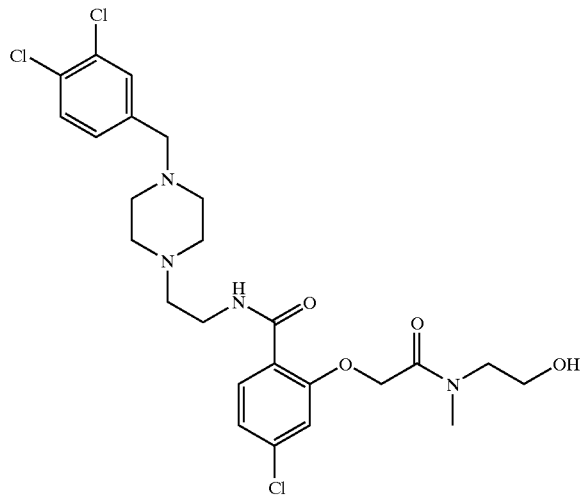

M.S. APCI (+ve) Base Peak 556.

EXAMPLE 22

2-[2-(4-Acetyl-1-piperazinyl)-2-oxoethoxy]-4-chloro-N-{2-[4-3.4-dichlorobenzyl)-1-piperazinyl]ethyl}benzamide

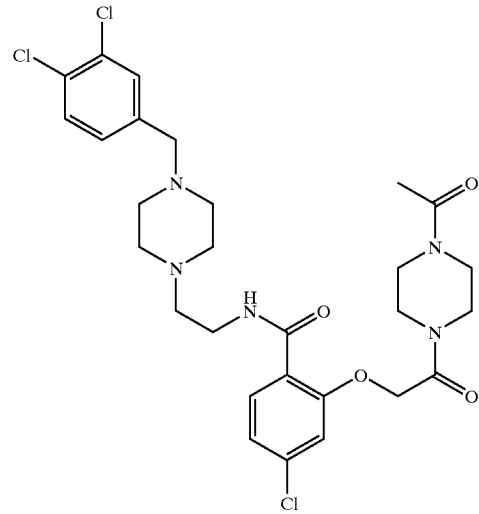

M.S. APCI (+ve) Base Peak 609.

EXAMPLE 23

4-Chloro-N-{2-[4-(3,4-dichlorobenzyl)-1-piperazinyl]ethyl}-2-{2-[ethyl(2-hydroxyethyl)amino]-2-oxoethoxy}benzamide

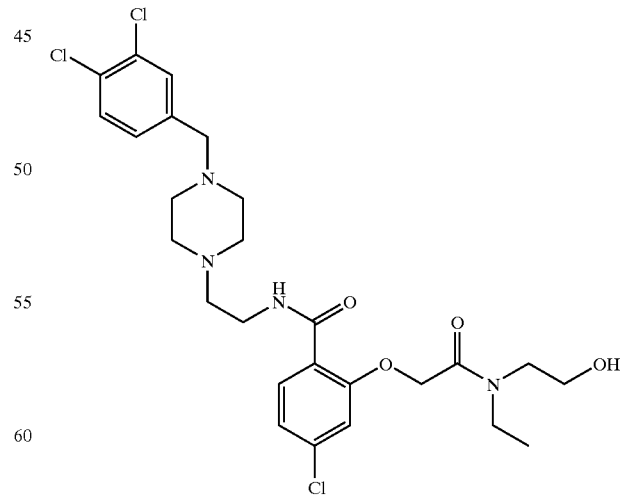

M.S. APCI (+ve) Base Peak 571.

EXAMPLE 24

4-Chloro-N-{2-[4-(3,4-dichlorobenzyl)-1-piperazinyl]ethyl}-2-(2-oxo-2-{[3-(2oxo-1-pyrrolidinyl)propyl]amino}ethoxy)benzamide

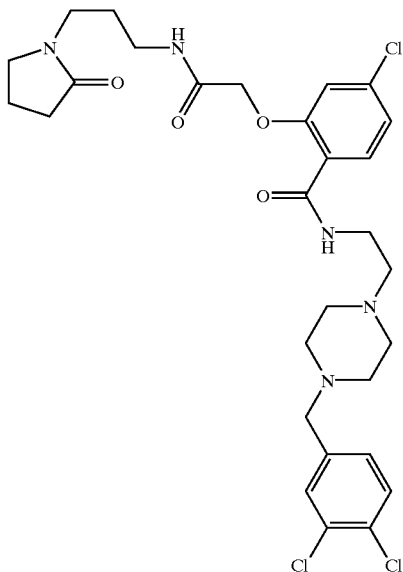

M.S. APCI (+ve) Base Peak 624.

EXAMPLE 25

Ethyl 1-(2-{5-chloro-2-[({2-[4-(3,4-dichlorobenzyl)-1-piperazinyl]ethyl}amino)carbonyl]phenoxy}acetyl)-4-piperidinecarboxylate

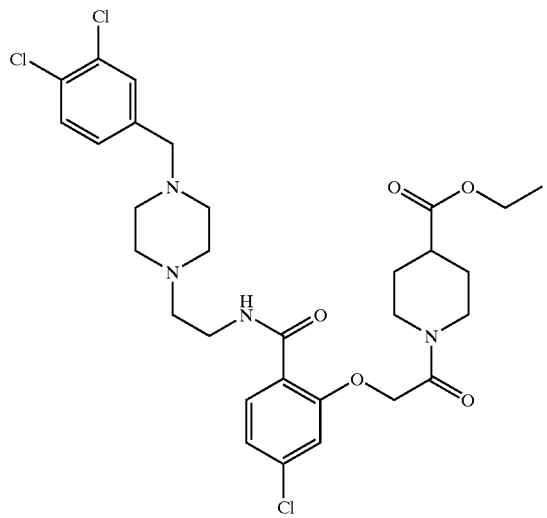

M.S. APCI (+ve) Base Peak 641.

EXAMPLE 26

Ethyl 1-(2-{5-chloro-2-[({2-[4-(3,4-dichlorobenzyl)-1-piperazinyl]ethyl}amino)carbonyl]phenoxy}acetyl)-3-piperidinecarboxylate

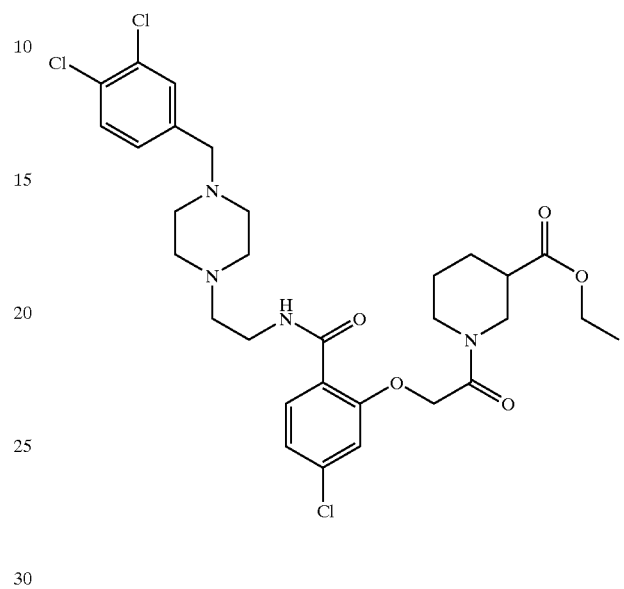

M.S. APCI (+ve) 639.

EXAMPLE 27

Methyl 2-[(2-{5-chloro-2-[({2-[4-(3,4-dichlorobenzyl)-1-piperazinyl]ethyl}amino)carbonyl]phenoxy}acetyl)amino]acetate

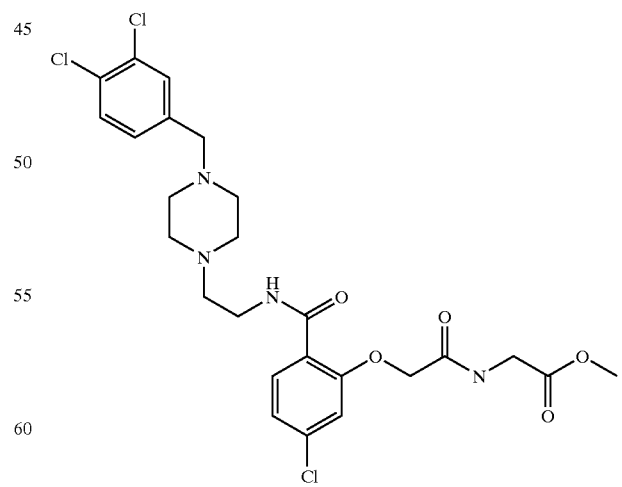

M.S. APCI (+ve) Base Peak 571.

EXAMPLE 28

4-Chloro-N-{2-[4-(3,4-dichlorobenzyl)-1-piperazinyl]ethyl}-2-(2-{[1-(hydroxymethyl)cyclopentyl]amino}-2-oxoethoxy)benzamide

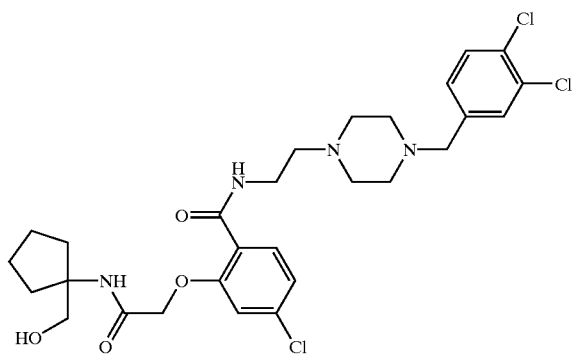

M.S. APCI (+ve) Base Peak 597.

EXAMPLE 29

4-Chloro-N-{2-[4-(3,4-dichlorobenzyl)-1-piperazinyl]ethyl}-2-(2-{[2-hydroxy-1-hydroxymethyl)ethyl]amino}-2-oxoethoxy)benzamide

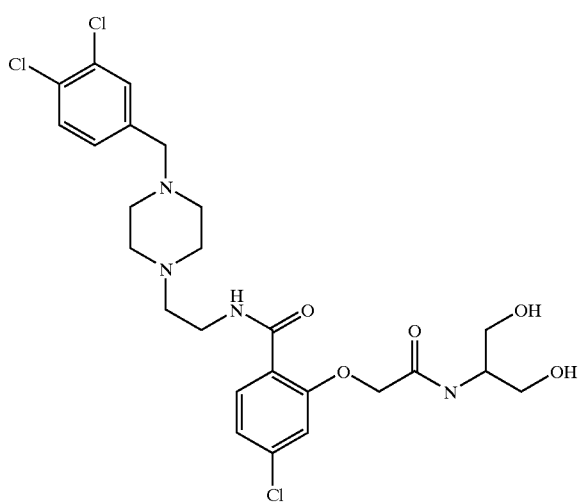

M.S. APCI (+ve) Base Peak 575.

EXAMPLE 30

1-(2-{5-Chloro-2-[({2-[4-(3,4-dichlorobenzyl)-1-piperazinyl]ethyl}amino)carbonyl]phenoxy}acetyl)-2-pyrrolidinecarboxamide

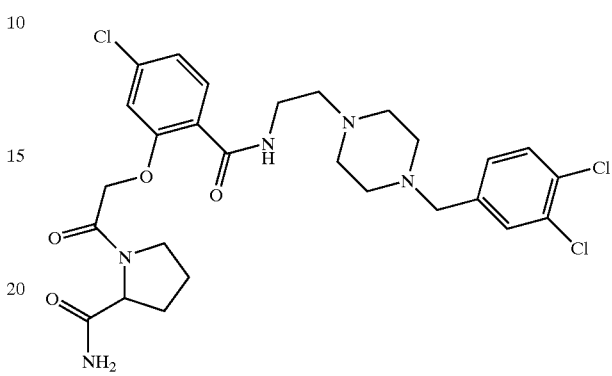

M.S. APCI (+ve) Base Peak 598.

EXAMPLE 31

4-Chloro-N-{2-[4-(3,4-dichlorobenzyl)-1-piperazinyl]ethyl}-2-{2-[4-(2-hydroxyethyl)-1-piperidinyl]-2-oxoethoxy}benzamide

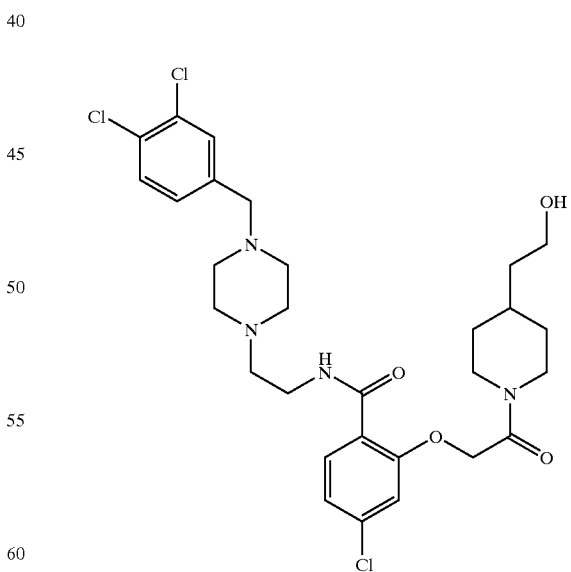

M.S. APCI (+ve) Base Peak 611.

EXAMPLE 32

4-Chloro-N-{2-[4-(3,4-dichlorobenzyl)-1-piperazinyl]ethyl}-2-[2-oxo-2-(2-propynylamino)ethoxy]benzamide

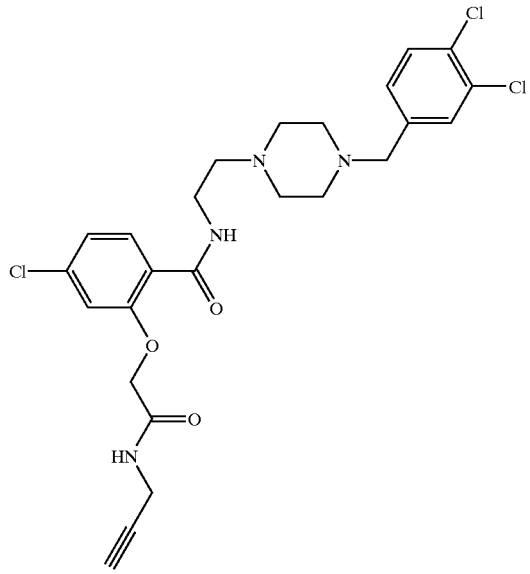

M.S. APCI (+ve) Base Peak 537.

EXAMPLE 33

4-Chloro-N-{2-[4-(3,4-dichlorobenzyl)-1-piperazinyl]ethyl}-2-[2-(4-methyl-1,4-diazepan-1-yl)-2-oxoethoxy]benzamide

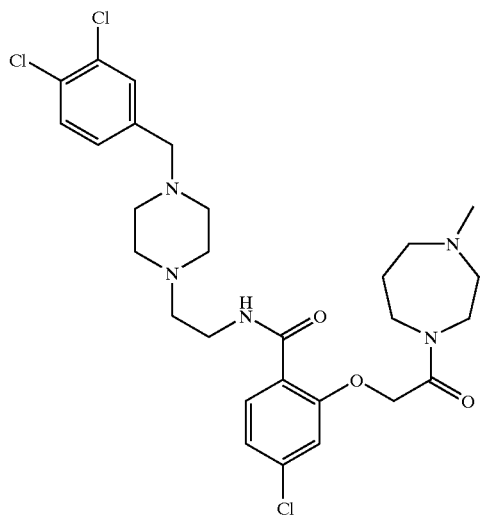

M.S. APCI (+ve) Base Peak 596.

EXAMPLE 34

4-Chloro-N-{2-[4-(3,4-dichlorobenzyl)-1-piperazinyl]ethyl}-2-(2-{[1-(hydroxymethyl)propyl]amino}-2-oxoethoxy)benzamide

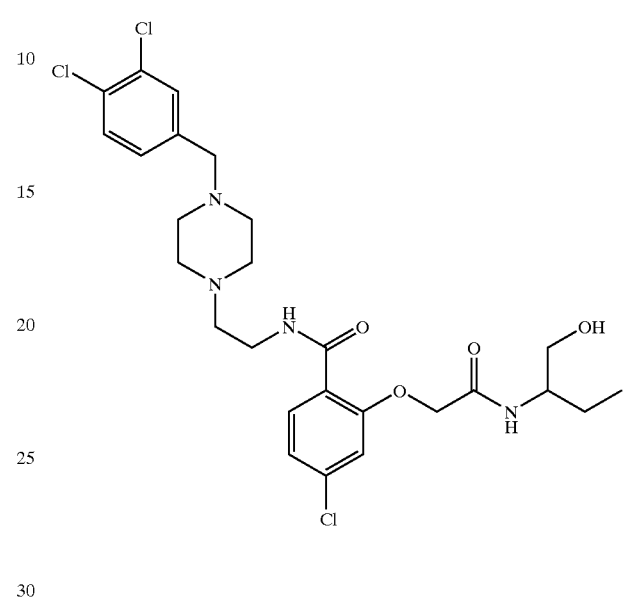

M.S. APCI (+ve) Base Peak 571.

EXAMPLE 35

4-Chloro-N-{2-[4-(3,4-dichlorobenzyl)-1-piperazinyl]ethyl}-2-[2-oxo-2-(1-piperazinyl)ethoxy]benzamide

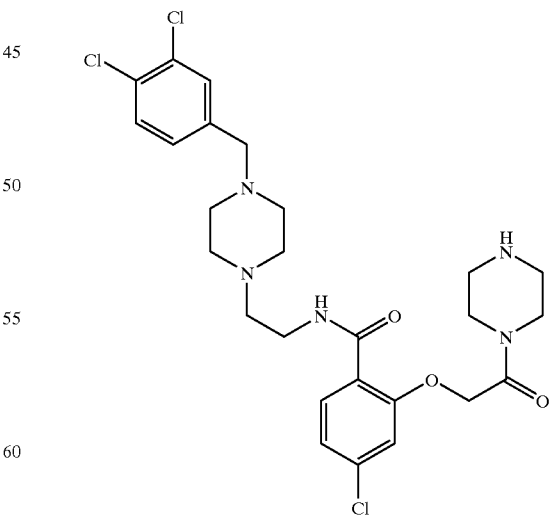

M.S. APCI (+ve) Base Peak 570.

EXAMPLE 36

N-[2-(4-Benzyl-1-piperazinyl)ethyl]-4-chloro-2-[2-(dimethylamino)-2-oxoethoxy]benzamide

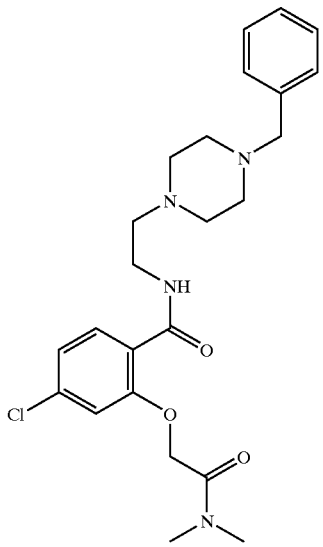

A solution of the amine prepared in Example 1(d) was dissolved in N,N-dimethylformamide and triethylamine and the benzyl halide were added. After 24 hours the solvent was evaporated to give the product as an oil.

M.S. APCI (+ve) Base Peak 459.

Following the general method of Example 36 and using the appropriate benzyl halide, the compounds of Examples 37 to 46 were prepared.

EXAMPLE 37

4-Chloro-2-[2-(dimethylamino)-2-oxoethoxyl]-N-{2-[4-(4-fluorobenzyl)-1-piperazinyl]ethyl}benzamide

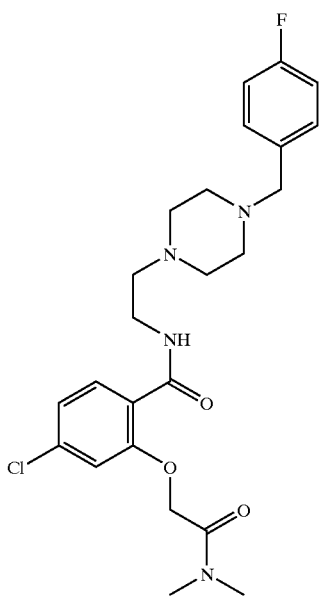

M.S. APCI (+ve) Base Peak 477.

EXAMPLE 38

4-Chloro-2-[2-(dimethylamino)-2-oxoethoxy]-N-{2-[4-(4-methylbenzyl)-1-piperazinyl]ethyl}benzamide

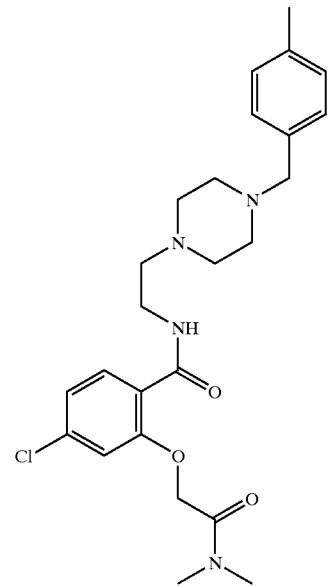

M.S. APCI (+ve) Base Peak 473.

EXAMPLE 39

4-Chloro-N-{2-[4-(4-chlorobenzyl)-1-piperazinyl]ethyl}-2-[2-(dimethylamino)-2-oxoethoxy]benzamide

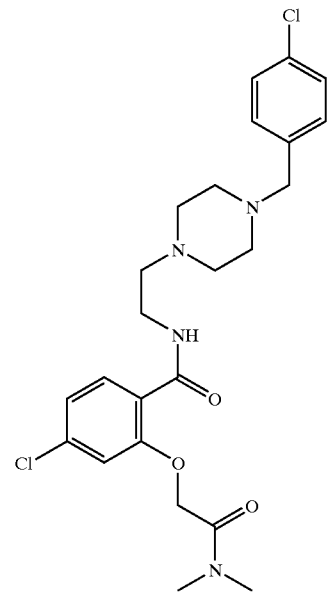

M.S. APCI (+ve) Base Peak 493.

EXAMPLE 40

4-Chloro-2-[2-(dimethylamino)-2-oxoethoxy]-N-{2-[4-(3,4-dimethylbenzyl)-1-piperazinyl]ethyl}benzamide

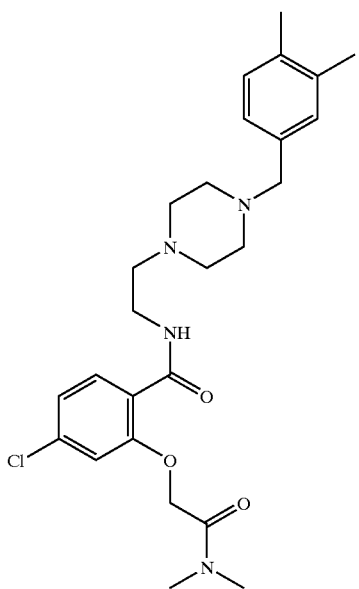

M.S. APCI (+ve) Base Peak 528.

EXAMPLE 41

4-Chloro-N-{2-[4-(4-cyanobenzyl)-1-piperazinyl]ethyl}-2-[2-(dimethylamino)-2-oxoethoxy]benzamide

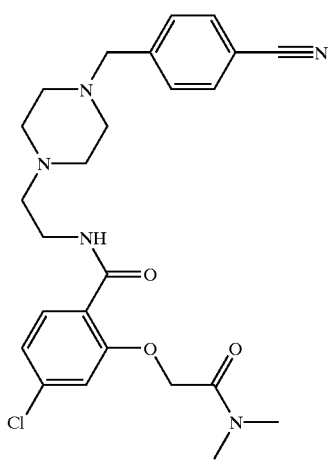

M.S. APCI (+ve) Base Peak 484.

EXAMPLE 42

4-Chloro-N-{2-[4-(3-cyanobenzyl)-1-piperazinyl]ethyl}-2-[2-(dimethylamino)-2-oxoethoxy]benzamide

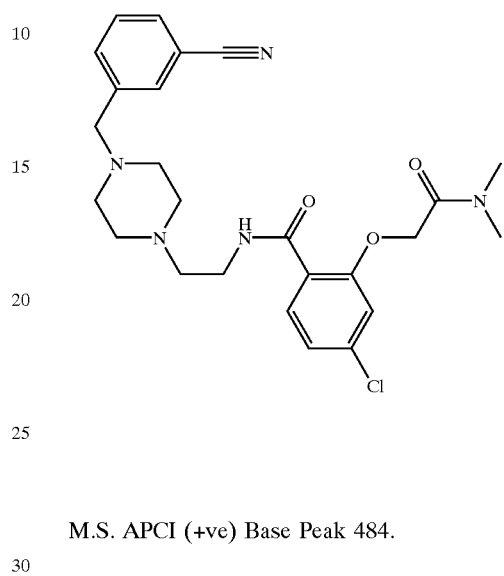

M.S. APCI (+ve) Base Peak 484.

EXAMPLE 43

4-Chloro-N-{2-[4-(3-chlorobenzyl)-1-piperazinyl]ethyl}-2-[2-(dimethylamino)-2-oxoethoxy]benzamide

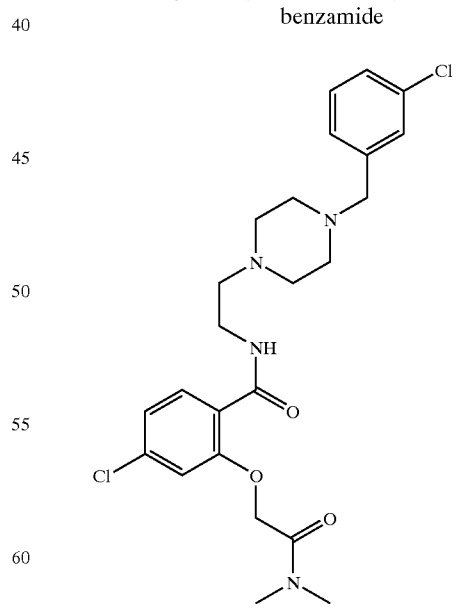

M.S. APCI (+ve) Base Peak 494.

EXAMPLE 44

4-Chloro-N-{2-[4-(2,3-dichlorobenzyl)-1-piperazinyl]ethyl}-2-[2-dimethylamino)-2-oxoethoxy]benzamide

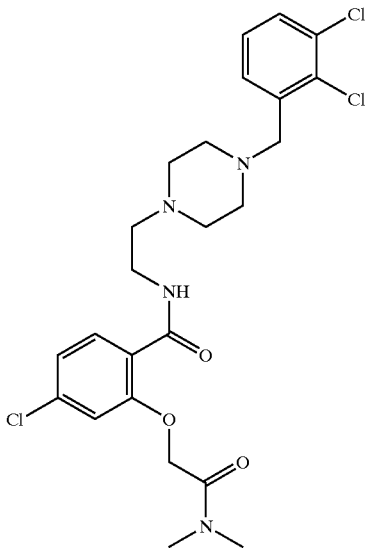

M.S. APCI (+ve) Base Peak 528.

EXAMPLE 45

4-Chloro-2-[2-(dimethylamino)-2-oxoethoxy]-N-{2-[4-(2,3,4-trifluorobenzyl)-1-piperazinyl]ethyl}benzamide

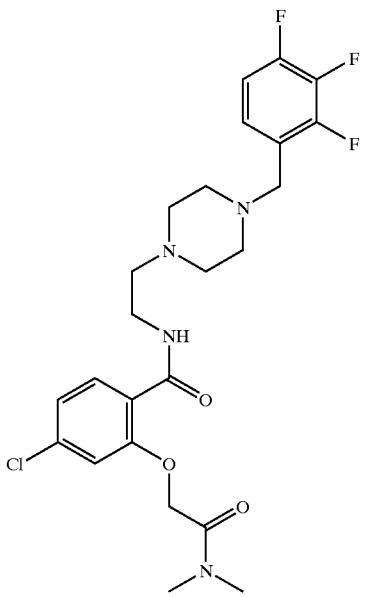

M.S. APCI (+ve) Base Peak 513.

EXAMPLE 46

4-Chloro-2-[2-(dimethylamino)-2-oxoethoxy]-N-{2-[4-(2,4,5-trifluorobenzyl)-1-piperazinyl]ethyl}benzamide

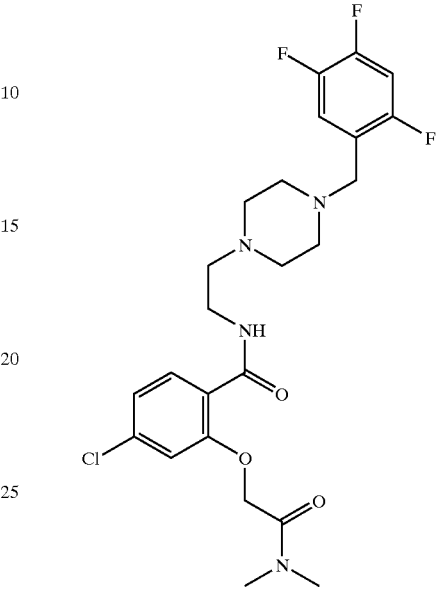

M.S. APCI (+ve) Base Peak 513.

PHARMACOLOGICAL ANALYSIS

Calcium flux $[Ca^{2+}]_i$ assay a) Human Eosinophils

Human eosinophils were isolated from EDTA anticoagulated peripheral blood as previously described (Hansel et al., *J. Immunol. Methods*, 1991, 145, 105–110). The cells were resuspended (5×10$^6$ ml$^{-1}$) and loaded with 5μM FLUO-3/AM+Pluronic F127 2.2 μ/ml (Molecular Probes) in low potassium solution (LKS; NaCl 118 mM, MgSO$_4$ 0.8 mM, glucose 5.5 mM, Na$_2$CO$_3$ 8.5 mM, KCl 5 mM, HEPES 20 mM, CaCl$_2$ 1.8 mM, BSA 0.1%, pH 7.4) for one hour at room temperature. After loading, cells were centrifuged at 200 g for 5 min and resuspended in LKS at 2.5×10$^6$ ml$^{-1}$. The cells were then transferred to 96 well FLIPr plates (Poly-D-Lysine plates from Becton Dickinson pre-incubated with 5 μM fibronectin for two hours) at 100 ml/well. The plate was centrifuged at 200 g for 5 min and the cells were washed twice with LKS (200 μl; room temperature).

A compound of the Examples was pre-dissolved in DMSO and added to a final concentration of 0.1%(v/v) DMSO. Assays were initiated by the addition of an A$_{50}$ concentration of eotaxin and the transient increase in fluo-3 fluorescence (1$_{Ex}$=490 nm and 1$_{Em}$=520 nm) monitored using a FLIPR (Fluorometric Imaging Plate Reader, Molecular Devices, Sunnyvale, U.S.A.).

b) Human Monocytes

Human monocytes were isolated from EDTA anticoagulated peripheral blood as previously described (Cunoosamy & Holbrook, *J. Leukocyte Biology*, 1998, S2, 13). Cells were resuspended (5×10$^6$ ml$^{-1}$) in LKS and loaded with 5 μM FLUO-3/AM+Pluronic F127 2.2μl/ml (Molecular Probes) for one hour at room temperature. After loading, cells were centrifuged at 200 g for 5 min and resuspended in LKS at 0.5×10$^6$ ml$^{-1}$. The cells were then transferred to 96 well FLIPr plates (Costar). To each well 100 µl of cells were added at a concentration of 0.5×10⁶ ml⁻¹. The plates were centrifuged (200 g; 5 mins; room temperature) to allow the cells to adhere. After centrifugation the cells were washed twice with LKS (200 µl; room temperature).

A compound of the Examples was pre-dissolved in DMSO and added to a final concentration of 0.1%(v/v) DMSO. Assays were initiated by the addition of an $A_{50}$ concentration of MIP-1α and the transient increase in fluo-3 fluorescence ($1_{EX}$=490 nm and $1_{Em}$=520 nm) monitored using a FLIPR (Fluorometric Imaging Plate Reader, Molecular Devices, Sunnyvale, U.S.A.).

The compounds of the Examples were found to be antagonists of the eotaxin mediated $[Ca^{2+}]_i$ in human eosinophils and/or antagonists of the MIP-1α mediated $[Ca^{2+}]_i$ in human monocytes.

Human Eosinophil Chemotaxis

Human eosinophils were isolated from EDTA anticoagulated peripheral blood as previously described (Hansel et al., *J. Immunol. Methods*, 1991, 145, 105–110). The cells were resuspended at 10×10⁶ ml⁻¹ in RPMI containing 200 IU/ml penicillin, 200 µg/ml streptomycin sulphate and supplemented with 10% HIFCS, at room temperature.

Eosinophils (700 µl) were pre-incubated for 15 mins at 37° C. with 7 µl of either vehicle or compound (100× required final concentration in 10% DMSO). The chemotaxis plate (ChemoTx, 3 µm pore, Neuroprobe) was loaded by adding 28 µl of a concentration of eotaxin (0.1 to 100 nM) containing a concentration of a compound according to the Examples or solvent to the lower wells of the chemotaxis plate. The filter was then placed over the wells and 25 µl of eosinophil suspension were added to the top of the filter. The plate was incubated for 1 hr at 37° C. in a humidified incubator with a 95% air/5% $CO_2$ atmosphere to allow chemotaxis.

The medium, containing cells that had not migrated, was carefully aspirated from above the filter and discarded. The filter was washed once with phosphate buffered saline (PBS) containing 5 mM EDTA to remove any adherent cells. Cells that had migrated through the filter were pelleted by centrifugation (300×g for 5 mins at room temperature) and the filter removed and the supernatant transferred to each well of a 96-well plate (Costar). The pelleted cells were lysed by the addition of 28 µl of PBS containing 0.5% Triton x100 followed by two cycles of freeze/thawing. The cell lysate was then added to the supernatant. The number of eosinophils migrating was quantified according to the method of Strath et al., *J. Immunol. Methods*, 1985, 83, 209 by measuring eosinophil peroxidase activity in the supernatant.

Certain compounds of the Examples were found to be antagonists of the eotaxin mediated human eosinophil chemotaxis.

What is claimed is:

1. A compound of general formula (I)

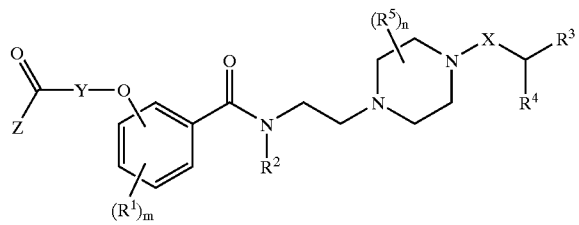

(I)

wherein:

each $R^1$ represents a substituent independently selected from halogen, C1 to 6 alkyl, C1 to 6 alkoxy, amino, nitro, cyano, $SO_2NH_2$, C1 to 6 haloalkyl, C1 to 6 haloalkoxy and C1 to 6 alkylsulphonyl;

m represents an integer 0 to 2;

$R^2$ represents hydrogen or C1 to 4 alkyl;

$R^3$ and $R^4$ independently represent hydrogen, C1 to 4 alkyl or phenyl; each phenyl group being optionally substituted by one or more substituents chosen independently from halogen, amino, nitro, cyano, C1 to 6 alkyl, C1 to 6 alkoxy, $SO_3H$, $SO_2NH_2$, C1 to 6 haloalkyl, C1 to 6 haloalkoxy and C1 to 6 alkylsulphonyl;

each $R^5$ independently represents hydrogen or C1 to 4 alkyl;

n represents an integer 0 to 4;

X represents a bond or C1 to 4 alkyl;

Y represents C1 to 4 alkyl;

Z represents OH or $NR^6R^7$;

$R^6$ and $R^7$ independently represent hydrogen, C1 to 6 alkyl, C2 to 6 unsaturated alkyl; each alkyl group being optionally substituted by one or more substituents independently chosen from hydroxyl, C1 to 4 alkoxy, amino, $NR^8R^9$, 1-pyrrolidin-2-onyl and $CO_2R^{10}$;

or the group $NR^6R^7$ together represents a 5 to 7 membered saturated or unsaturated azacyclic ring system optionally incorporating one or two further heteroatoms independently selected from N, O and S; said ring system being optionally further substituted by $CO_2R^{11}$, $COR^{12}$, $CONR^{13}R^{14}$ or C1 to 4 alkyl; said alkyl group itself being optionally further substituted by hydroxyl; and $R^8$, $R^9$, $R^{10}$, $R^{11}$, $R^{12}$, $R^{13}$ and $R^{14}$ independently represent hydrogen or C1 to 4 alkyl; or a pharmaceutically acceptable salt thereof.

2. A compound according to claim 1 wherein X represents a bond.

3. A compound according to claim 1 or claim 2, wherein $R^1$ represents chloro and m is 1.

4. A compound according to any one of claims 1 to 3, wherein Z represents $NR^6R^7$.

5. A compound according to any one of the preceding claims, wherein Y represents $CH_2$.

6. A compound according to any one of the preceding claims, wherein each $R^5$ represents hydrogen.

7. A compound of formula (I), or a pharmaceutically acceptable salt thereof, according to claim 1 being selected from:

4-chloro-2-[2-(dimethylamino)-2-oxoethoxy]-N-[2-(4-phenethyl-1-piperazinyl)ethyl]benzamide;

2-{5-chloro-2-[({2-[4-(3,4-dichlorobenzyl)-1-piperazinyl]ethyl}amino)carbonyl]phenoxy}acetic acid;

4-chloro-N-{2-[4-(3,4-dichlorobenzyl)-1-piperazinyl]ethyl}-2-[2-dimethylamino)-2 oxoethoxy]benzamide;

4-chloro-N-{2-[4-(3,4-dichlorobenzyl)-1-piperazinyl]ethyl}-2-{2-[(2-hydroxy-1-methylethyl)amino]-2-oxoethoxy}benzamide;

4-chloro-N-{2-[4-(3,4-dichlorobenzyl)-1-piperazinyl]ethyl}-2-{2-[(2-hydroxy-1,1-dimethylethyl)amino]-2-oxoethoxy}benzamide;

4-chloro-N-{2-[4-(3,4-dichlorobenzyl)-1-piperazinyl]ethyl}-2-[2-(methylamino)-2-oxoethoxy]benzamide;

4-chloro-N-{2-[4-(3,4-dichlorobenzyl)-1-piperazinyl]ethyl}-2-[2-oxo-2-(1-pyrrolidinyl)ethoxy]benzamide;

2-(2-amino-2-oxoethoxy)-4-chloro-N-{2-[4-(3,4-dichlorobenzyl)-1-piperazinyl]ethyl}benzamide;
4-chloro-N-(2-{4-[1-(4-chlorophenyl)ethyl]-1-piperazinyl}ethyl)-2-[2-(dimethylamino)-2-oxoethoxy]benzamide;
4-chloro-N-{2-[4-(3,4-dichlorobenzyl)-1-piperazinyl]ethyl}-2-[2-dimethylamino)-2-oxoethoxy]benzamide;
4-chloro-N-{2-[4-(3,4-dichlorobenzyl)-1-piperazinyl]ethyl}-2-{[2-(dimethylamino)ethyl](methyl)amino]-2-oxoethoxy}benzamide;
2-[(2-{5-chloro-2-[({2-[4-(3,4-dichlorobenzyl)-1-piperazinyl]ethyl}amino)carbonyl]phenoxy}acetyl)amino]acetic acid;
4-chloro-N-{2-[4-(3,4-dichlorobenzyl)-1-piperazinyl]ethyl}-2-[2-(dimethylamino)-2-oxoethoxy]-N-methylbenzamide;
N-[2-(4-benzhydryl-1-piperazinyl)ethyl]-4-chloro-2-[2-(dimethylamino)-2-oxoethoxy]benzamide;
4-chloro-2-[2-(dimethylamino)-2-oxoethoxy]-N-{2-[4-(4-fluorobenzyl)-2,5-dimethyl-1-piperazinyl]ethyl}benzamide;
E-4-chloro-N-{2-[4-(3,4-dichlorobenzyl)-2,5-dimethyl-1-piperazinyl]ethyl}-2-[2-(dimethylamino)-2-oxoethoxy]benzamide;
4-chloro-N-{2-[4-(3,4-dichlorobenzyl)-1-piperazinyl]ethyl}-2-{2-[4-(2-hydroxyethyl)-1-piperazinyl]-2-oxoethoxy}benzamide;
4-chloro-N-{2-[4-(3,4-dichlorobenzyl)-1-piperazinyl]ethyl}-2-[2-(4-morpholinyl)-2-oxoethoxy]benzamide;
4-chloro-N-{2-[4-(3,4-dichlorobenzyl)-1-piperazinyl]ethyl}-2-{2-[(2-methoxyethyl)amino]-2-oxoethoxy}benzamide;
4-chloro-N-{2-[4-(3,4-dichlorobenzyl)-1-piperazinyl]ethyl}-2-{2-[3-(hydroxymethyl)-1-piperidinyl]-2-oxoethoxy}benzamide;
4-chloro-N-{2-[4-(3,4-dichlorobenzyl)-1-piperazinyl]ethyl}-2-{2-[(2-hydroxyethyl)(methyl)amino]-2-oxoethoxy}benzamide;
2-[2-(4-acetyl-1-piperazinyl)-2-oxoethoxy]-4-chloro-N-{2-[4-(3,4-dichlorobenzyl)-1-piperazinyl]ethyl}benzamide;
4-chloro-N-{2-[4-(3,4-dichlorobenzyl)-1-piperazinyl]ethyl}-2-{2-[ethyl(2-hydroxyethyl)amino]-2-oxoethoxy}benzamide;
4-chloro-N-{2-[4-(3,4-dichlorobenzyl)-1-piperazinyl]ethyl}-2-(2-oxo-2-{[3-(2-oxo-1-pyrrolidinyl)propyl]amino}ethoxy)benzamide;
ethyl 1-(2-{5-chloro-2-[({2-[4-(3,4-dichlorobenzyl)-1-piperazinyl]ethyl}amino)carbonyl]phenoxy}acetyl)-4-piperidinecarboxylate;
ethyl 1-(2-{5-chloro-2-[({2-[4-(3,4-dichlorobenzyl)-1-piperazinyl]ethyl}amino)carbonyl]phenoxy}acetyl)-3-piperidinecarboxylate;
methyl 2-[(2-{5-chloro-2-[({2-[4-(3,4-dichlorobenzyl)-1-piperazinyl]ethyl}amino)carbonyl]phenoxy}acetyl)amino]acetate;
4-chloro-N-{2-[4-(3,4-dichlorobenzyl)-1-piperazinyl]ethyl}-2-(2-{[1-(hydroxymethyl)cyclopentyl]amino}-2-oxoethoxy)benzamide;
4-chloro-N-{2-[4-(3,4-dichlorobenzyl)-1-piperazinyl]ethyl}-2-(2-{[2-hydroxy-1-(hydroxymethyl)ethyl]amino}-2-oxoethoxy)benzamide;
1-(2-{5-chloro-2-[({2-[4-(3,4-dichlorobenzyl)-1-piperazinyl]ethyl}amino)carbonyl]phenoxy}acetyl)-2-pyrrolidinecarboxamide;
4-chloro-N-{2-[4-(3,4-dichlorobenzyl)-1-piperazinyl]ethyl}-2-{2-[4-(2-hydroxyethyl)-1-piperidinyl]-2-oxoethoxy}benzamide;
4-chloro-N-{2-[4-(3,4-dichlorobenzyl)-1-piperazinyl]ethyl}-2-[2-oxo-2-(2-propynylamino)ethoxy]benzamide;
4-chloro-N-{2-[4-(3,4-dichlorobenzyl)-1-piperazinyl]ethyl}-2-[2-(4-methyl-1,4-diazepan 1-yl)-2-oxoethoxy]benzamide;
4-chloro-N-{2-[4-(3,4-dichlorobenzyl)-1-piperazinyl]ethyl}-2-(2-{[1-(hydroxymethyl)propyl]amino}-2-oxoethoxy)benzamide;
4-chloro-N-{2-[4-(3,4-dichlorobenzyl)-1-piperazinyl]ethyl}-2-[2-oxo-2-(1-piperazinyl)ethoxy]benzamide;
N-[2-(4-benzyl-1-piperazinyl)ethyl]-4-chloro-2-[2-(dimethylamino)-2-oxoethoxy]benzamide;
4-chloro-2-[2-(dimethylamino)-2-oxoethoxy]-N-{2-[4-(4-fluorobenzyl)-1-piperazinyl]ethyl}benzamide;
4-chloro-2-[2-(dimethylamino)-2-oxoethoxy]-N-{2-[4-(4-methylbenzyl)-1-piperazinyl]ethyl}benzamide;
4-chloro-N-{2-[4-(4-chlorobenzyl)-1-piperazinyl]ethyl}-2-[2-(dimethylamino)-2-oxoethoxy]benzamide;
4-chloro-2-[2-(dimethylamino)-2-oxoethoxy]-N-{2-[4-(3,4-dimethylbenzyl)-1-piperazinyl]ethyl}benzamide;
4-chloro-N-{2-[4-(4-cyanobenzyl)-1-piperazinyl]ethyl}-2-[2-(dimethylamino)-2-oxoethoxy]benzamide;
4-chloro-N-{2-[4-(3-cyanobenzyl)-1-piperazinyl]ethyl}-2-[2-(dimethylamino)-2 oxoethoxy]benzamide;
4-chloro-N-{2-[4-(3-chlorobenzyl)-1-piperazinyl]ethyl)-2-[2-(dimethylamino)-2-oxoethoxy]benzamide;
4-chloro-N-{2-[4-(2,3-dichlorobenzyl)-1-piperazinyl]ethyl}-2-[2-(dimethylamino)-2-oxoethoxy]benzamide;
4-chloro-2-[2-(dimethylamino)-2-oxoethoxy]-N-(2-[4-(2,3,4-trifluorobenzyl)-1-piperazinyl]ethyl}benzamide;
4-chloro-2-[2-(dimethylamino)-2-oxoethoxy]-N-{2-[4-(2,4,5-trifluorobenzyl)-1-piperazinyl]ethyl}benzamide.

8. A process for the preparation of a compound of formula (I) as defined in claim 1 which comprises:

(i) reacting a compound of general formula (II)

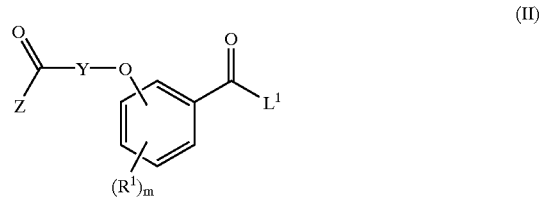

wherein $R^1$, m, Y and Z are as defined in formula (I) and $L^1$ represents a leaving group, with a compound of general formula (III)

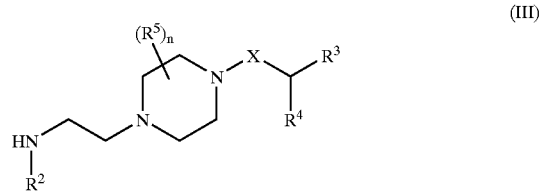

or an acid addition salt thereof, wherein $R^2$, $R^3$, $R^4$, $R^5$, X and n are as defined in formula (I); or (ii) reacting a compound of general formula (IV)

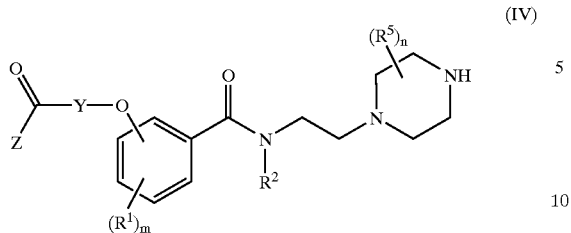

wherein $R^1$, $R^2$, $R^5$, Y, Z, m and n are as defined in formula (I), with a compound of general formula (V)

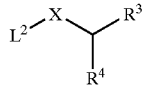

wherein $R^3$, $R^4$ and X are as defined in formula (I) and $L^2$ represents a leaving group; or (iii) when X represents $CH_2$, reacting a compound of general formula (IV)

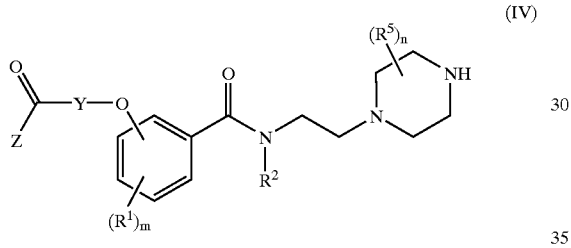

wherein $R^1$, $R^2$, $R^5$, Y, Z, m and n are as defined in formula (I), with a compound of general formula (VI)

wherein $R^3$ and $R^4$ are as defined in formula (I), using the process of reductive amination; or (iv) when Z represents $NR^6R^7$, reacting a compound of general formula (VII)

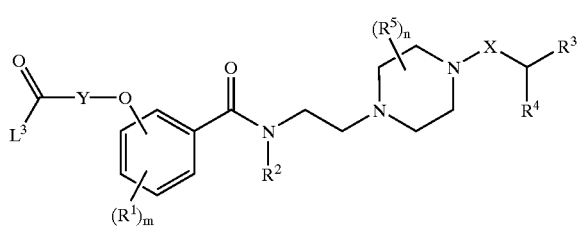

wherein $R^1$, $R^2$, $R^3$, $R^4$, $R^5$, X, Y, m and n are as defined in formula (I) and $L^3$ is a leaving group, with a compound of general formula (VIII)

wherein $R^6$ and $R^7$ are as defined in formula (I); or (v) reacting a compound of general formula (IX)

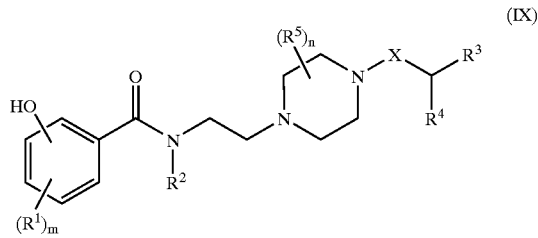

wherein $R^1$, $R^2$, $R^3$, $R^4$, $R^5$, X, m and n are as defined in formula (I), with a compound of formula (X)

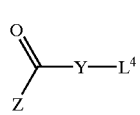

wherein Y and Z are as defined in formula (I) and $L^4$ is a leaving group; or (vi) reacting a compound of general formula (XI)

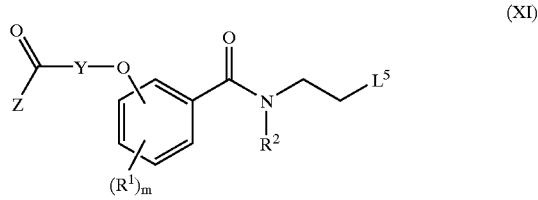

wherein $R^1$, $R^2$, Y, Z and m are as defined in formula (I) and $L^5$ is a leaving group, with a compound of formula (XII)

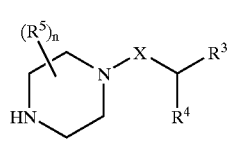

wherein $R^3$, $R^4$, $R^5$, X and n are as defined in formula (I); or (vii) preparing a compound of formula (I) wherein $R^2$ represents alkyl C1 to 4, by alkylation of a corresponding compound of formula (I) wherein $R^2$ represents hydrogen;

and optionally after (i), (ii), (iii), (iv), (v), (vi) or (vii) forming a pharmaceutically acceptable salt of the compound of formula (I) obtained.

9. A pharmaceutical composition comprising a compound of formula (I), or a pharmaceutically acceptable salt thereof, as claimed in any one of claims 1 to 7 in association with a pharmaceutically acceptable adjuvant, diluent or carrier.

10. A process for the preparation of a pharmaceutical composition as claimed in claim 9 which comprises mixing a compound of formula (I), or a pharmaceutically acceptable salt thereof, as claimed in any one of claims 1 to 7 with a pharmaceutically acceptable adjuvant, diluent or carrier.

11. A method of treating an inflammatory disease in a person suffering from, or at risk of, said disease, which comprises administering to the person a therapeutically effective amount of a compound of formula (I), or a pharmaceutically acceptable salt thereof, as claimed in any one of claims 1 to 7.

* * * * *

UNITED STATES PATENT AND TRADEMARK OFFICE
CERTIFICATE OF CORRECTION

PATENT NO.    : 6,562,825 B1
DATED         : May 13, 2003
INVENTOR(S)   : Baxter, Andrew J. G.

It is certified that error appears in the above-identified patent and that said Letters Patent is hereby corrected as shown below:

<u>Title page,</u>
Item [*] Notice, should read -- Subject to any disclaimer, the term of this patent is extended or adjusted under 35 U.S.C. 154 (b) by 34 days. --

Signed and Sealed this

Thirty-first Day of May, 2005

JON W. DUDAS
*Director of the United States Patent and Trademark Office*